United States Patent
Bull et al.

(10) Patent No.: US 10,633,630 B2
(45) Date of Patent: Apr. 28, 2020

(54) ACCELERATION OF *MYCOBACTERIUM* GROWTH

(71) Applicant: ST GEORGE'S HOSPITAL MEDICAL SCHOOL, London (GB)

(72) Inventors: Timothy John Bull, London (GB); Kai Hilpert, London (GB)

(73) Assignee: ST GEORGE'S HOSPITAL MEDICAL SCHOOL (GB)

( * ) Notice: Subject to any disclaimer, the term of this patent is extended or adjusted under 35 U.S.C. 154(b) by 203 days.

(21) Appl. No.: 15/319,987

(22) PCT Filed: Jun. 19, 2015

(86) PCT No.: PCT/GB2015/051801
§ 371 (c)(1),
(2) Date: Dec. 19, 2016

(87) PCT Pub. No.: WO2015/193688
PCT Pub. Date: Dec. 23, 2015

(65) Prior Publication Data
US 2017/0121672 A1 May 4, 2017

(30) Foreign Application Priority Data
Jun. 20, 2014 (GB) .................................. 1411075.3

(51) Int. Cl.
*C12N 1/20* (2006.01)
*C07K 7/06* (2006.01)
*C12Q 1/02* (2006.01)
*C12Q 1/04* (2006.01)

(52) U.S. Cl.
CPC .................. *C12N 1/20* (2013.01); *C07K 7/06* (2013.01); *C12Q 1/025* (2013.01); *C12Q 1/04* (2013.01); *G01N 2800/26* (2013.01); *G01N 2800/56* (2013.01)

(58) Field of Classification Search
None
See application file for complete search history.

(56) References Cited

U.S. PATENT DOCUMENTS

2006/0078979 A1 4/2006 Whitlock
2011/0160125 A1 6/2011 Deol et al.

FOREIGN PATENT DOCUMENTS

| RU | 2215039 | 10/2003 |
| RU | 2233876 | 8/2004 |
| WO | 9960016 | 11/1999 |
| WO | 0245736 | 6/2002 |
| WO | WO2002-45736 | * 6/2002 |
| WO | 2006050611 | 5/2006 |
| WO | 2011002860 | 1/2011 |
| WO | 2013053772 | 4/2013 |

OTHER PUBLICATIONS

Mahalakshmi et al. ("The use of D-Amino acids in Peptide Design";Chapter 5.9; D:amino acids; A New Frontier in Amino Acid and Protein Research; 2006).*
LifeTein (<https://www.lifetein.com/Peptide-Synthesis-D-Amino-Acid.html> available online May 2012; Accessed Nov. 26, 2018).*
Bull et al., "Improved culture medium (TiKa) for *Mycobacterium avium* subspecies *paratuberculosis* (MAP) matches qPCR sensitivity and reveals significant proportions of non-viable MAP in lymphoid tissue of vaccinated MAP challenged animals," 2017, Frontiers in Microbiology, 7:1-8.
Cherkasov et al., "Use of artificial intelligence in the design of small peptide antibiotics effective against a broad spectrum of highly antibiotic-resistant superbugs," 2008, ACS Chemical Biology 4(1) 65-74.
Fjell et al., "Identification of novel antibacterial peptides by chemoinformatics and machine learning," 2009, Journal Med. Chem. 52(7):2006-2015.
Haney et al., "Peptide design for antimicrobial and immunomodulatory applications", 2013, Peptide Science 100(6): 572-583.
Hilpert et al., "High-throughput generation of small antibacterial peptides with improved activity," 2005, Nature Biotechnology 23(8):1008-1012.
Hilpert et al., "Sequence requirements and an optimization strategy for short antimicrobial peptides," 2006, Chemistry & Biology 13:1101-1107.
Knappe et al., "Easy strategy to protect antimicrobial peptides from fast degradation in serum," 2010, Antimicrobial Agents and Chemotherapy 54(9):4003-4005.
Mikut et al., "Improving short antimicrobial peptides despite elusive rules for activity," 2016, Biochimica et Biophysica Acta (BBA)—Biomembranes 1858:1024-1033.
Ramón-García et al., "Targeting *Mycobacterium tuberculosis* and other microbial pathogens using improved synthetic antibacterial peptides," 2013, Antimicrobial Agents and Chemotherapy 57(5):2295-2303.
Zhang et al., "Resuscitation of dormant *Mycobacterium tuberculosis* by phospholipids or specific peptides," 2001, Biochemical and Biophysical Research Communications 284(2):542-547.
International Application No. PCT/GB2015/051801, International Search Report dated Oct. 1, 2015.
International Application No. PCT/GB2015/051801, Written Opinion dated Oct. 1, 2015.

* cited by examiner

*Primary Examiner* — James H Alstrum-Acevedo
*Assistant Examiner* — Tara L Martinez
(74) *Attorney, Agent, or Firm* — Kilpatrick Townsend & Stockton LLP

(57) ABSTRACT

The invention is in the field of growth of Mycobacteria. In particular, agents have been identified which enhance the growth of Mycobacterial species, which are naturally slow-growing. Such agents can therefore be used in the identification of Mycobacteria and in the diagnosis of Mycobacterial infections.

14 Claims, 6 Drawing Sheets
Specification includes a Sequence Listing.

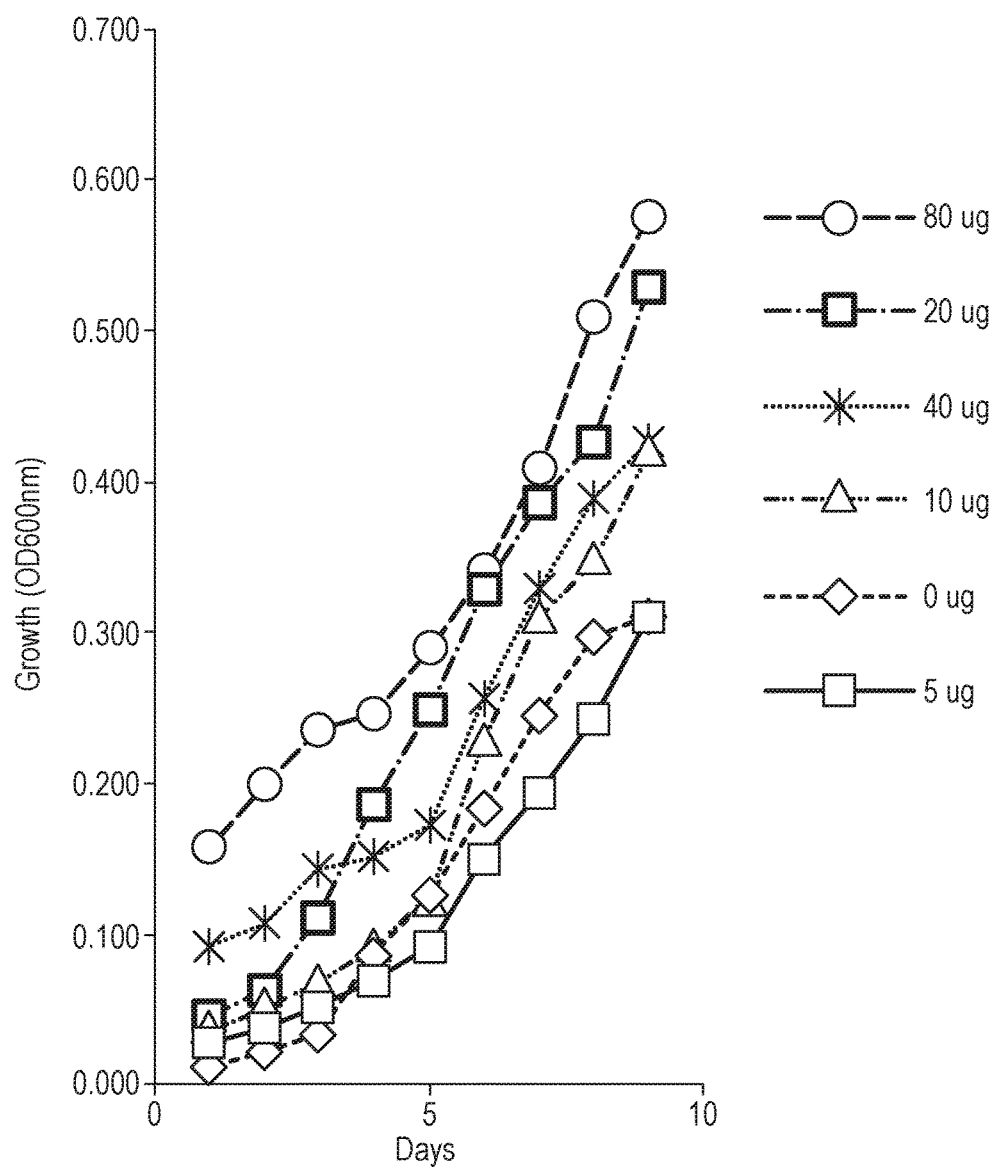

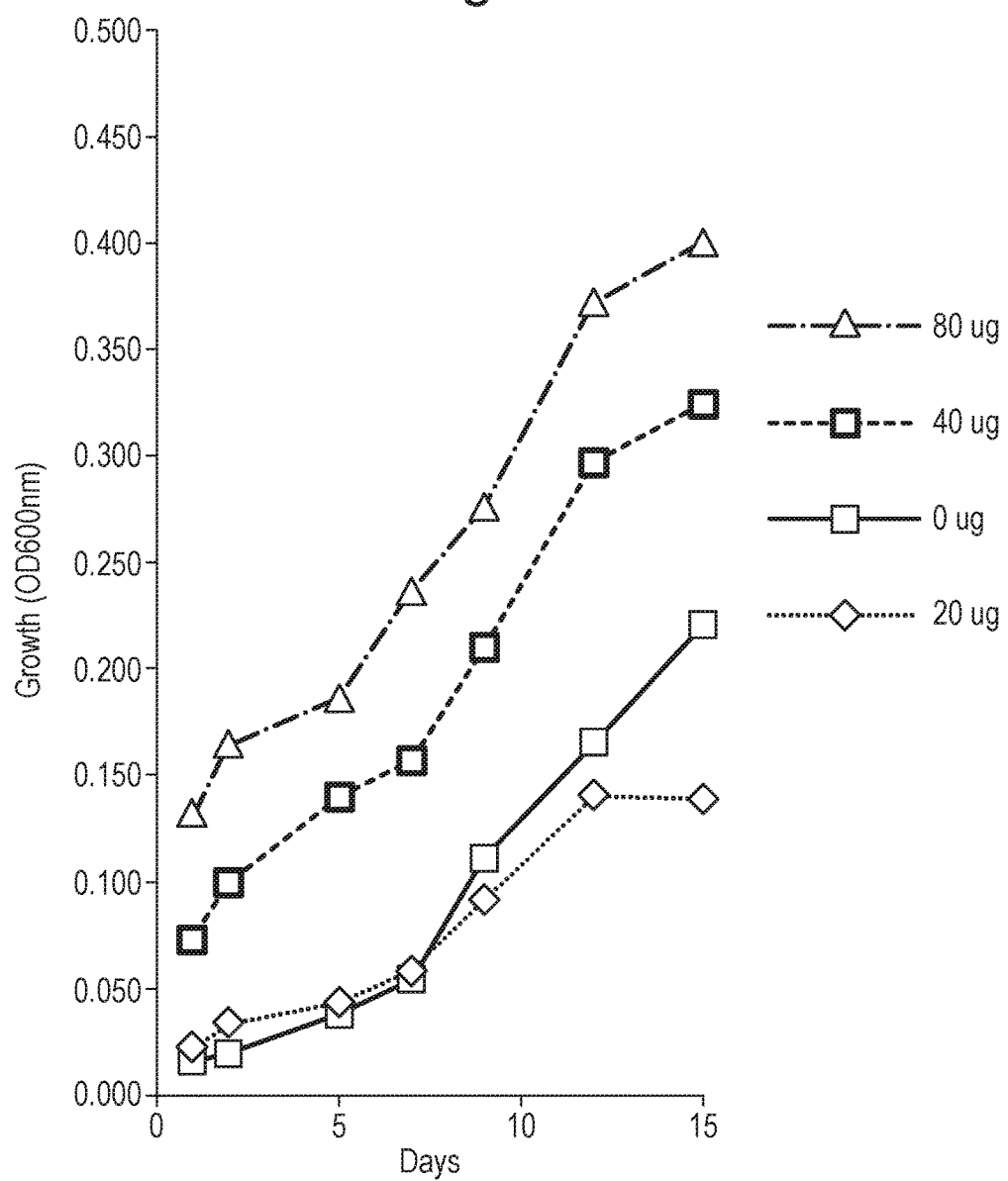

Fig. 6
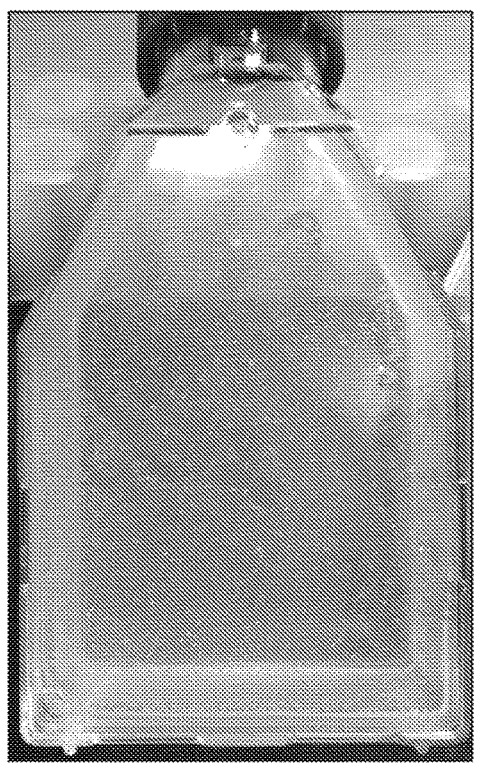 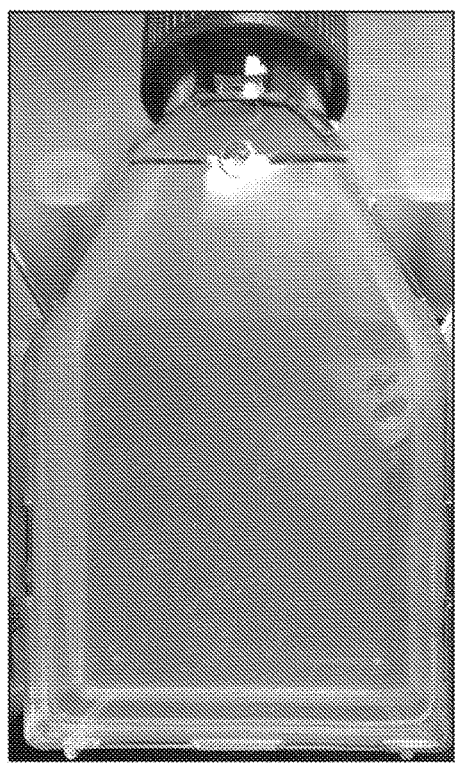
POZ-A culture with Tika14D    POZ-A culture only

ACCELERATION OF *MYCOBACTERIUM* GROWTH

CROSS REFERENCE TO RELATED APPLICATIONS

This application is a national stage application under 35 U.S.C. § 371 of PCT/GB2015/051801 filed Jun. 19, 2015, which claims priority to United Kingdom Application No. 1411075.3 filed Jun. 20, 2014. The disclosures of each of these applications are hereby incorporated by reference herein in their entireties.

FIELD OF THE INVENTION

The invention relates to a method of enhancing the growth of cells of a slow-growing Mycobacterial species. The invention also relates to a method for diagnosing a suspected slow-growing Mycobacterial species infection, and for monitoring the progress of such an infection. Kits for use in the methods are also provided, together with a screening method for new peptides.

BACKGROUND OF THE INVENTION

The World Health Organisation estimates that over ⅓ of the world's population are latently infected with Mycobacteria. More than 60 million people are tested for Mycobacterial infections each year. Initial investigations and follow up of latent and multidrug resistant infections costs £1.5 billion worldwide, with treatment of UK cases of multidrug resistant Mycobacterial infections costing up to £7,000 per patient.

Culture of a pathogen from an appropriate patient sample is still the gold standard for diagnosis. Despite over 100 years of development in Mycobacteria culture methodology, producing growth is frustratingly slow (up to six weeks), inaccurate and particularly in samples with low numbers of pathogens, can be impossible. This is because, as adapted intracellular human pathogens, Mycobacteria are able to stop dividing and become dormant on entry into the host. Initiating Mycobacterial re-growth from patient samples to obtain a diagnosis is not assured. Those proportions of bacteria that do begin growing often require many weeks, sometimes months, to generate observable growth. This slow detection time is detrimental to effective national health strategies dealing with Mycobacterial disease; it has led to culture methods being of only retrospective worth. Until now, simple reproducible methods or stable preparations able to achieve reliable growth stimulation have not been identified.

SUMMARY OF THE INVENTION

The present inventors have surprisingly found that certain peptides which are able to act as antimicrobials are also able to enhance the growth of cells of a slow-growing Mycobacterial species. The invention thus provides a method of enhancing growth of such a species, comprising culturing the cells in a growth medium comprising the peptide. The invention also provides methods of identifying a Mycobacterial species and diagnosing a suspected slow-growing Mycobacterial species infection in a subject, comprising growing cells of the slow-growing Mycobacterial species in a growth medium comprising the peptide. Furthermore, the invention provides methods for monitoring the progress of a slow-growing Mycobacterial species infection in a subject.

In particular, the invention provides a method of enhancing the growth of cells of a slow-growing Mycobacterial species, comprising culturing the cells in a growth medium comprising a cationic antimicrobial peptide, which peptide:
(a) is from 6 to 50 amino acids in length;
(b) includes one or more positively charged residues; and
(c) comprises at least 20% hydrophobic residues.

The invention also provides:
a method of diagnosing a suspected slow-growing Mycobacterial species infection in a subject, said method comprising:
  (a) obtaining a sample from the subject suspected of having such an infection;
  (b) growing cells of the slow-growing Mycobacterial species from the sample by culturing the cells in a growth medium comprising one or more cationic antimicrobial peptides as defined above; and
  (c) identifying the Mycobacterial species, subspecies and/or antibiotic resistance after growth of the cells, and thereby diagnosing the infection;
a method of monitoring the progress of a slow-growing Mycobacterial species infection in a subject, said method comprising:
  (a) obtaining a sample from the subject known to have such an infection;
  (b) culturing cells from the sample in a growth medium comprising one or more cationic antimicrobial peptides as defined above;
  (c) analysing growth of the cells, or the characteristics of the cells after growth; and
  (d) repeating steps (a), (b) and (c);
use of a cationic antimicrobial peptide as defined above for enhancing growth of cells of a slow-growing Mycobacterial species;
a kit comprising one or more peptides as defined above, and instructions for performing the methods as defined above; and
a method of screening for a peptide which enhances the growth of cells of a slow-growing Mycobacterial species, said method comprising culturing cells of the slow-growing Mycobacterial species in a growth medium comprising the peptide and monitoring growth of the cells, wherein the peptide is:
  (a) from 6 to 50 amino acids in length;
  (b) includes one or more positively charged amino acids; and
  (c) comprises at least 20% hydrophobic residues,
and providing an output that identifies the peptide as enhancing growth of the cells where the peptide reduces the lag phase and/or increases the division rate of the cells compared with growth of the cells in a culture medium in the absence of any peptide.

DESCRIPTION OF THE FIGURES

FIG. 5 shows growth curves at various concentrations of peptide. Part (A) presents results for the TiKa 14D peptide and part (B) presents results for the TiKa 102 peptide.

FIG. 6 shows solid POZ-A medium with and without 20 μg/ml TiKa 14D inoculated in parallel with identical inocula of *Mycobacterium avium* subspecies *paratuberculosis* and incubated for 2 weeks at 37° C.

DESCRIPTION OF THE SEQUENCE LISTING

Figure 1:
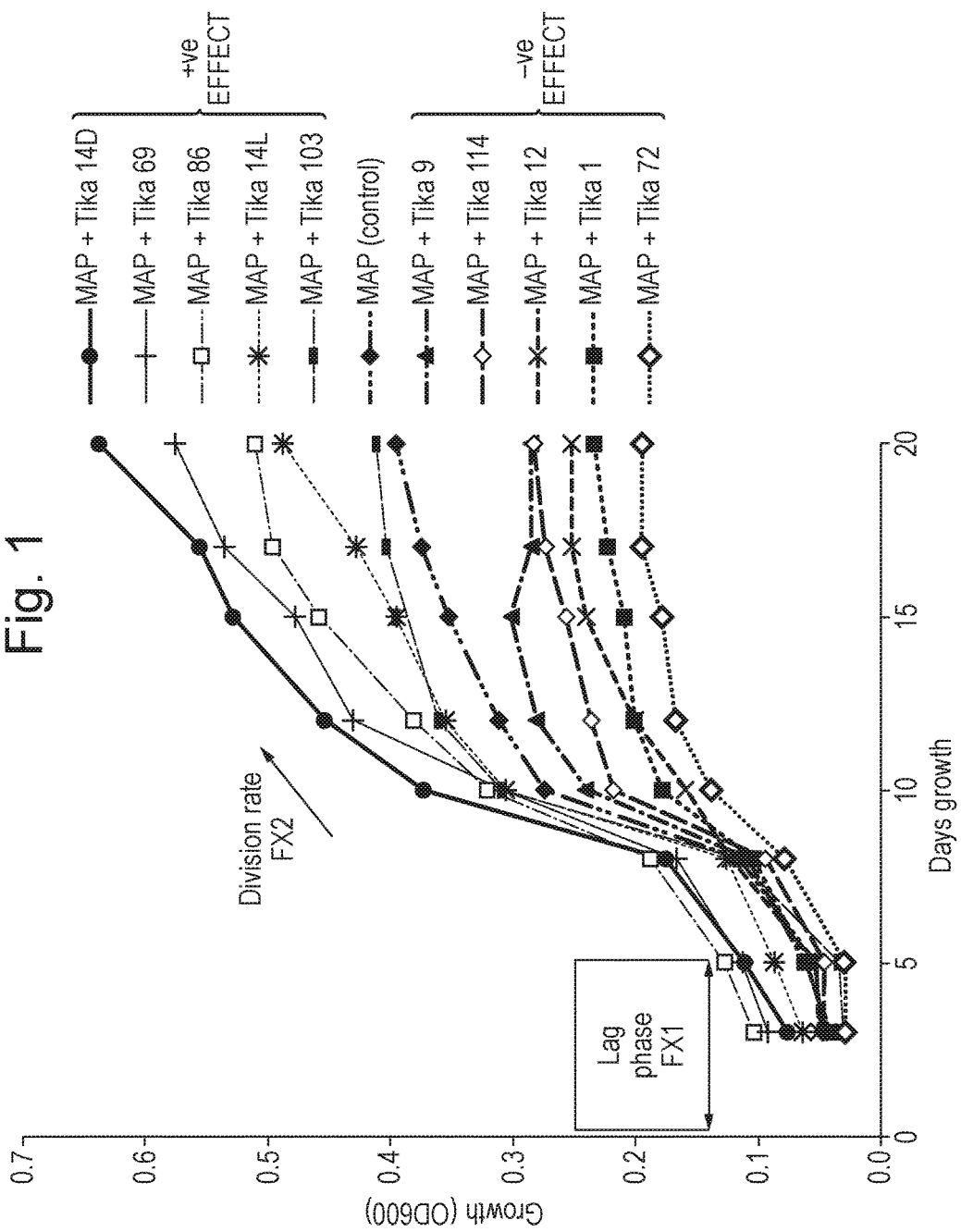
FIG. 1 shows variation in effects induced over a 20 day period on *Mycobacterium avium* subspecies *paratuberculosis* (MAP) cultures by various TiKa supplements (antimicrobial peptides) added at 20 μg/ml (final). FX1=reduction in lag phase, FX2=increase in division rate.

SEQ ID NOs: 1-117 show the sequences of peptides tested for their ability to enhance Mycobacterial growth (presented in the Appendix).

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an amino acid sequence" includes two or more such sequences, and the like.

All publications, patents and patent applications cited herein, whether supra or infra, are hereby incorporated by reference in their entirety.

Method of Enhancing Growth of Mycobacterial Cells

The present invention relates to a method of enhancing (accelerating) the growth of cells of a slow-growing Mycobacterial species. Bacterial growth in culture can typically be modelled in four phases. These are: the lag phase, where the bacteria adapts to growth conditions before dividing; the exponential phase, which is characterised by rapid doubling (division); the stationary phase; and the death phase. In the method of the present invention, enhancement of growth of the cells of the Mycobacterial species typically results from a reduction in the lag phase, or an increase in the division rate during the exponential phase. Preferably, the lag phase is reduced and the division rate of the bacteria is increased. In particular, the lag phase is reduced and/or the division rate of the bacteria is increased compared with an identical control which lacks the antimicrobial peptide.

In some cases, the lag phase may be reduced by at least 25% or preferably by at least 50% compared with an identical control which lacks the antimicrobial peptide. Furthermore, in some cases the division rate of the bacteria is increased at least 1.5 fold, preferably at least 2 fold compared with an identical control which lacks the antimicrobial peptide.

As discussed further below, antimicrobial peptides have been shown to kill Gram negative bacteria, Gram positive bacteria, enveloped viruses, fungi and even transformed cancerous cells. In the present invention, the antimicrobial peptides have a direct effect on accelerating growth of a slow-growing Mycobacterial species. In other words, the antimicrobial peptides enhance growth of the slow-growing Mycobacterial species when the Mycobacterial species is cultured in the absence of other microorganisms. The antimicrobial peptides may directly reduce the lag phase and/or increase the division rate of the bacteria.

Nevertheless, the antimicrobial peptide may also have an indirect effect on enhancing growth of the Mycobacterial species. For example, in a mixed culture of bacteria the antimicrobial peptide may kill contaminating bacteria, viruses etc in addition to directly enhancing growth of the slow-growing Mycobacterial species in question.

The lag phase and division rate can be determined using routine methods in the art. Typically, growth and expansion of cells of a bacterial culture is determined by monitoring the optical density (OD) of the culture (e.g. the $OD_{600}$ or the $OD_{800}$ as illustrated in the Examples section below). The lag phase and the division rate can be determined from plots of the OD over time.

In the method of the invention, the growth of cells of a slow-growing Mycobacterial species is enhanced. Slow-growing Mycobacteria can be defined as species of Mycobacteria which take more than 7 days to form colonies clearly visible to the naked eye on subculture (e.g. on one or more of the media listed below at 37° C.). The method of the invention may be used to accelerate growth of any slow-growing Mycobacterial species. Examples of such species are *Mycobacterium tuberculosis, Mycobacterium avium, Mycobacterium bovis Mycobacterium leprae* and *Mycobacterium kanasasii*. Preferably, in the method of the invention the slow-growing Mycobacterial species is *Mycobacterium tuberculosis, Mycobacterium avium, Mycobacterium bovis* or *Mycobacterium leprae*.

The *Mycobacterium avium* may be any subspecies, particularly *Mycobacterium avium* subspecies *paratuberculosis, Mycobacterium avium* subspecies *silvaticum, Mycobacterium avium* subspecies *hominissuis* or *Mycobacterium avium* subspecies *avium*.

The method comprises culturing the cells of the slow-growing Mycobacterial species in a growth medium. The growth medium may be any solid or liquid growth medium capable of supporting growth of a particular species. Such media are known in the art. The liquid medium may, for example, be BacTAlert MP medium (Biomerieux, France); MGIT960 medium (Becton Dickinson, USA); Middlebrook 7H9 modified medium (reference: Pozzato et al. J. Microbiol. Methods. 2011 March; 84(3):413-7)); or Middlebrook 7H9 modified medium plus 0.5% sodium pyruvate (Sigma, UK). An example of a suitable solid medium is POZ-A medium: Middlebrook 7H9 modified medium (as above) with added 1.6% electrophoresis agarose (Sigma, UK).

The other conditions under which the bacteria are cultured may be any appropriate conditions for growth of a particular species or subspecies. Such conditions are well known in the art. For example, cultures of Mycobacteria are typically incubated at 37° C.

In the method, the cells of the slow-growing Mycobacterial species may be from a sample of a subject suspected of having an infection with such a species. The subject is typically human, but may also be an animal (e.g. a domestic animal, a livestock animal or a wild animal). Exemplary animals include ruminants, rabbits, bison, cats, dogs and badgers.

The cells may also be from a sample of non-human/animal origin that is suspected of being infected. In other words, in some circumstances the subject may be non-human or animal. For example, the sample may be a food or liquid sample, a water sample (e.g. from a reservoir) or another environmental sample (e.g. a soil sample).

In the case of human or animal subjects, the subject may have presented with symptoms indicating that they have a Mycobacterial infection. Alternatively, the subject may be tested as part of a screening programme.

The cells may also be from a sample of a subject known to have a slow-growing Mycobacterial infection. In this case, the subject has first been diagnosed with the Mycobacterial infection. Diagnosis may have been achieved based on standard clinical techniques. Diagnosis may also have involved growing cells from an initial sample from the subject in culture in the absence of presence of a peptide described herein.

The sample from the subject may be any appropriate sample, depending on the suspected infection. For a human or animal subject the sample may be sputum, pus, cerebrospinal fluid, skin, blood, urine and/or faeces. The sample could also be from the gut mucosa and/or lymph node tissue. The sample is preferably a respiratory sample.

When the subject is an animal (such as a livestock animal), the sample may be a milk sample. Furthermore, if the subject is non-human/animal, the sample may simply be an extract of the subject.

Methods for obtaining such samples are well known in the art.

Typically, with a subject suspected of having an infection, the number of cells of the slow-growing Mycobacterial species in the initial sample from the subject is too small to allow determination of the bacterial species, subspecies, or antibiotic resistance. In other words, the number of cells is too small to allow diagnosis of the infection. For this reason, the number cells of the initial sample from the subject is generally increased (via inoculation of culture medium, incubation and subsequent growth of the cells) in order to allow identification and diagnosis. Identification of the bacterial species, subspecies and/or antibiotic resistance can be determined after growth and expansion of the cells using routine methods known in the art.

The method of the present invention therefore provides means for the number of cells of the Mycobacteria to be amplified more rapidly, thus allowing quicker identification of the species, subspecies, and/or antibiotic resistance. The method of the present invention thus provides for a more rapid diagnosis of a slow-growing Mycobacterial species infection.

The method of the present invention may also allow progress of a slow-growing Mycobacterial species infection in a subject to be monitored. In this case, the subject is first diagnosed as having an infection with a slow-growing Mycobacterial species. As discussed above, this may be achieved using standard clinical techniques and typically involves obtaining a sample from the subject, growing cells from the sample in a growth medium, and identifying the species or subspecies after growth of the cells. The cells may be grown in a medium either in the absence or presence of a peptide described herein.

After diagnosis, the subject is treated using antimycobacterial agents. Suitable agents used to treat each Mycobacterial species are well known in the art and include for example Isoniazid, Rifamycin, Pyrazinamide, Ethambutol, Para-amino salicylic acid, Streptomycin, Kanamycin, Ethionamide, Capreomycin, Cycloserine, Fluoroquinolones, Ciprofloxacin, Sparfloxacin, Ofloxacin, Dapsone, Clofazimine and Macrolides.

After treatment with an appropriate agent (or combination of agents), the method of the invention may then be used to monitor progress of the infection. In other words, to monitor whether treatment with the agent is effective. In this scenario, at appropriate time points after treatment with the agent(s), a further sample is obtained from the subject and the cells from the sample cultured in a growth medium comprising a peptide described herein. Appropriate time points for obtaining a sample from a subject can readily be determined by a clinician. Samples may be obtained, for example, 1, 2, 3, 4, 5, 6 or 7 days after initiation of the treatment.

Growth of the cells, or the characteristics of the cells, are analysed in order to determine the progress of the infection. If no growth of cells is observed in the culture medium this is indicative that treatment with the agent(s) has been successful. Alternatively, characteristics of the cells, such as antibiotic resistance, may be analysed in order to monitor progress of the infection.

Typically, the process of obtaining a sample of cells from a subject, culturing the cells in a growth medium comprising a peptide described herein, and analysing growth of the cells or characteristics of the cells, is repeated until successful treatment of the infection. Again, samples may be obtained at any appropriate interval such as every 1, 2, 3 4, 5, 6, 7 or 14 days.

Although the method of the invention may be used for the purposes of identification of Mycobacteria, diagnosis of infections, and monitoring progress of infections, other uses may also be contemplated. For example, the method may be used to more rapidly provide greater numbers of slow-growing Mycobacterial cells in the laboratory for use in subsequent experiments.

Antimicrobial Peptides

The method of the present invention comprises culturing the cells of a slow-growing Mycobacterial species in a growth medium comprising a cationic antimicrobial peptide. The peptide is (a) from 6 to 50 amino acids in length, (b) includes one or more positively charged residues, and (c) comprises at least 20% hydrophobic residues.

Antimicrobial peptides (also called host defence peptides) are part of the innate immune response and are found among all classes of life. Fundamental differences exist between prokaryotic and eukaryotic cells that may represent targets for antimicrobial peptides. Antimicrobial peptides are a very diverse group of different sequences, showing different modes of action. Many of these peptides are potent, broad spectrum antibiotics which demonstrate potential as novel therapeutic agents. Antimicrobial peptides have been demonstrated to kill Gram negative and Gram positive bacteria (including strains that are resistant to conventional antibiotics), enveloped viruses, fungi and even transformed or cancerous cells. Unlike the majority of conventional antibiotics it appears as though antimicrobial peptides may also have the ability to enhance immunity by functioning as immunomodulators.

Several bioinformatic databases exist to catalogue antimicrobial peptides such as CAMP (Collection of sequences and structures of antimicrobial peptides), CAMP release 2, the Antimicrobial Peptide Database, LAMP and BioPD.

The term "cationic" reflects the fact that the peptide has an isoelectric point of greater than about 9.

As discussed further below, the peptide is from 6 to 50 amino acids in length, includes one or more positively charged residue and comprises at least 20% hydrophobic residues. Except for these requirements, the composition of the peptide is not limited provided that the peptide has ability to enhance the growth of slow-growing Mycobacteria. The ability of peptides to act in this way can tested using growth curves, as described above. In particular, a peptide may be identified as capable of enhancing growth of a slow-growing Mycobacterial species if it decreases the lag phase and/or increases the division rate of the bacteria.

In the method of the invention, the antimicrobial peptide is from 6 to 50 amino acids in length. The antimicrobial peptide may be from 6 to 20 amino acids in length. Preferably the antimicrobial peptide is from 8 to 15 amino acids in length. More preferably, the antimicrobial peptide is from 9 to 13 amino acids in length.

The peptide includes one or more, preferably two or more, positively charged residues. The properties of the 20 main amino acids are defined in table 1 below. As shown in the Table, Arginine (R), lysine (K) and histidine (H) are positively charged residues. Furthermore, ornithine is a charged residue that may be present in peptides. The charged amino acids in the peptides described herein are preferably arginine or lysine.

The peptide may include, for example, 1, 2, 3, 4, 5, 6, 7, 8, 9, 10 or 20 positively charged amino acids. Preferably, the peptide comprises at least 25% positively charged amino acids. The peptide may comprise at least 25%, at least 30%, at least 35%, at least 40%, at least 45%, at least 50%, at least 55%, at least 60%, at least 65%, at least 70%, or at least 75% positively charged residues (provided the peptide retains at least 20% hydrophobic residues). Again, these positively charged residues are preferably arginine or lysine.

In other words, the peptide may comprise from 25% to 80% positively charged residues. The peptide may preferably comprise from 25% to 60% positively charged residues, from 25% to 55% positively charged residues, or from 25% to 50% positively charged residues. The peptide more preferably comprises from 30% to 60% positively charged residues, from 30% to 55% positively charged residues, or most preferably from 30% to 50% positively charged residues.

TABLE 1

| Chemical properties of amino acids | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

The peptide also comprises at least 20% hydrophobic residues. As shown in Table 1, alanine (A), cysteine (C), phenylalanine (F), isoleucine (I), leucine (L), methionine (M), proline (P), valine (V), tryptophan (W) and tyrosine (Y) are all hydrophobic. In the peptide, the hydrophobic residues are preferably tryptophan, isoleucine, valine and/or phenylalanine.

Preferably, the peptide comprises at least 25%, 30%, 35%, 40%, 45%, 50%, 55%, 60%, 65%, 70% or 75% hydrophobic residues. The peptide typically comprises from 40% to 65%, from 40% to 70% or from 40% to 75% hydrophobic residues. The peptide more preferably comprises from 45% to 65%, from 45% to 70%, or from 45% to 75% hydrophobic residues.

The peptide typically comprises at least one isoleucine residue, at least one valine residue and/or at least one arginine residue. Tryptophan may also be present.

The peptide may comprise the sequence WKIVFWWRR (SEQ ID NO: 14). The sequence may, for example, have at least one residue added at one or both ends of SEQ ID NO: 14, provided that the peptide retains its ability to enhance growth of the slow-growing Mycobacteria. The peptide may have for example 1, 2, 3, 4 or 5 residues added at one or both ends of the sequence. Equally, the peptide may have residues deleted from SEQ ID NO: 14 provided that the activity of the peptide is not affected.

The peptide may also consist of the sequence of SEQ ID NO: 14.

The peptide may comprise or consist of a variant or SEQ ID NO: 14. The variant typically retains the same proportion (percentage) of positively charged residues and hydrophobic residues. The positively charged residues and hydrophobic residues may be any of those described above. The variant preferably retains the same proportion of arginine, lysine, tryptophan, isoleucine, valine and/or phenylalanine residues.

The variant may retain hydrophobic residues at positions corresponding to residues 1, 3, 4, 5, 6 and 7 of SEQ ID NO: 14, and positively charged residues at positions corresponding to residues 2, 8 and 9 of SEQ ID NO: 14. For example, in a variant where 2 amino acids are added at the start of SEQ ID NO: 14, the variant will preferably contain hydrophobic residues at positions 3, 5, 6, 7, 8 and 9, and positively charged residues at positions 4, 10 and 11. Any changes in the sequence of the variant relative to SEQ ID NO: 14 are then typically conservative substitutions.

Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 above. Where amino acids have similar polarity, this can also be determined by reference to the hydropathy scale for amino acid side chains in Table 2.

Typically seen as conservative substitutions are the replacements, one for another, among the aliphatic amino acids Ala, Val, Leu and Phe; interchange of the hydroxyl residues Ser and Thr; exchange of the acidic residues Asp and Glu; substitution between the amide residues Asn and Gln; exchange of the basic residues Lys and Arg; and replacements among the aromatic residues Phe, Tyr.

TABLE 2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

Most preferably, the variant of SEQ ID NO: 14 retains tryptophan residues at positions corresponding to positions 1, 6 and 7 of SEQ ID NO 14, and arginine residues at positions corresponding to positions 8 and 9 of SEQ ID NO: 14. Any substitutions relative to SEQ ID NO: 14 may then be conservative substitutions.

As discussed above, any variant must still retain the ability to enhance growth of slow-growing Mycobacteria.

Alternatively, the peptide may comprise the sequence RRWRIVVIRVRR (SEQ ID NO: 69). As described above, the sequence may have at least one residue added at one or both ends of SEQ ID NO: 69, provided that the peptide retains its ability to enhance growth of the slow-growing Mycobacteria. The peptide may have, for example, 1, 2, 3, 4 or 5 residues added at one or both ends of the sequence. Furthermore, residues may be deleted from the sequence provided that the peptide's ability to enhance growth is not affected.

The peptide may also consist of the sequence of SEQ ID NO: 69.

The peptide may comprise or consist of a variant or SEQ ID NO: 69. Variants may be as described above for SEQ ID NO: 14. The variant typically retains the same proportion (percentage) of positively charged residues and hydrophobic residues. The positively charged residues and hydrophobic residues may be any of those described above. The variant preferably retains the same proportion of arginine, tryptophan, isoleucine and/or valine residues.

The variant may retain hydrophobic residues at positions corresponding to residues 3, 5, 6, 7, 8 and 10 of SEQ ID NO: 69, and positively charged residues at positions corresponding to residues 1, 2, 4, 9, 11 and 12 of SEQ ID NO: 69. Any changes in the sequence of the variant relative to SEQ ID NO: 69 are typically conservative substitutions as described above.

More preferably, the variant retains arginine and tryptophan residues at positions corresponding to their position in SEQ ID NO: 69. For example, a variant will preferably retain a tryptophan residue at a position corresponding to position 3 of SEQ ID NO: 69, and arginine residues at positions corresponding to positions 1, 2, 4, 9, 11 and 12 of SEQ ID NO: 69.

Most preferably, any substitutions in the sequence are then conservative substitutions.

As a further alternative, the peptide may comprise the sequence RLARIVVIRVAR-BB-K (biotin) (SEQ ID NO: 103). As described below, the -BB-K (biotin) tag is beta-alanine, beta-alanine, modified lysine with biotin attached to the side chain.

The sequence may have at least one residue added at one or both ends of SEQ ID NO: 103, provided that the peptide retains its ability to enhance growth of the slow-growing Mycobacteria. The peptide may have, for example, 1, 2, 3, 4 or 5 residues added at one or both ends of the sequence. Furthermore, residues may be deleted from SEQ ID NO: 103 provided that activity of the peptide is retained.

The peptide may also consist of the sequence of SEQ ID NO: 103.

The peptide may also comprise or consist of a variant or SEQ ID NO: 103. Variants may be as described above. The variant typically retains the same proportion (percentage) of positively charged residues and hydrophobic residues. The positively charged residues and hydrophobic residues may be any of those described above. The variant preferably retains the same proportion of arginine, lysine, alanine, isoleucine and/or valine residues.

The variant may retain hydrophobic residues at positions corresponding to residues 2, 3, 5, 6, 7, 8, 10 and 11 of SEQ ID NO: 103, and positively charged residues at positions corresponding to residues 1, 4, 9 and 12 of SEQ ID NO: 103. Any changes in the sequence of the variant relative to SEQ ID NO: 103 are typically conservative substitutions as described above.

More preferably, the variant retains arginine residues at positions corresponding to their position in SEQ ID NO: 114. For example, a variant will preferably retain arginine residues at positions corresponding to residues 1, 4, 9 and 12 of SEQ ID NO: 103. Most preferably, any substitutions are then conservative substitutions.

The peptide may include any of the following non-natural amino acids:

1. Exemplary conservative variants of tryptophan
2. DL-7-azatryptophan
3. β-(3-benzothienyl)-L-alanine
4. β-(3-benzothienyl)-D-alanine
5. 5-benzyloxy-DL-tryptophan
6. 7-benzyloxy-DL-tryptophan
7. 5-bromo-DL-tryptophan
8. 5-fluoro-DL-tryptophan
9. 6-fluoro-DL-tryptophan
10. 5-hydroxy-L-tryptophan
11. 5-hydroxy-DL-tryptophan
12. 5-methoxy-DL-tryptophan
13. α-methyl-DL-tryptophan
14. 1-methyl-DL-tryptophan
15. 5-methyl-DL-tryptophan
16. 6-methyl-DL-tryptophan
17. 7-methyl-DL-tryptophan
18. D-1,2,3,4-tetrahydronorharman-3-carboxylic acid
19. DL-6-methoxy-1,2,3,4-tetrahydronorharman-1-carboxylic acid
20. 5-Hydroxytryptophan: 2-Amino 3-[5-hydroxyindolyl]-propionic acid
21. L-Neo-Tryptophan
22. D-Neo-Tryptophan
23. Exemplary conservative variants of phenylalanine and tyrosine
24. 4-aminomethyl)-L-phenylalanine
25. 4-aminomethyl)-D-phenylalanine
26. 4-amino-L-phenylalanine
27. 4-amino-D-phenylalanine 28. 3-amino-L-tyrosine
29. 4-bromo-L-phenylalanine
30. 4-bromo-D-phenylalanine
31. 4-bis(2-chloroethyl)amino-L-phenylalanine
32. 2-chloro-L-phenylalanine
33. 2-chloro-D-phenylalanine
34. 4-chloro-L-phenylalanine
35. 4-chloro-D-phenylalanine
36. 3-chloro-L-tyrosine
37. 3,4-dichloro-L-phenylalanine
38. 3,4-dichloro-D-phenylalanine
39. 3,4-difluoro-L-phenylalanine
40. 3,4-difluoro-D-phenylalanine
41. 3,4-dihydroxy-L-phenylalanine
42. 3,5-diiodo-L-thyronine
43. 3,5-diiodo-D-tyrosine
44. 3,4-dimethoxy-L-phenylalanine
45. 3,4-dimethoxy-DL-phenylalanine
46. O-ethyl-L-tyrosine
47. O-ethyl-D-tyrosine
48. 2-fluoro-L-phenylalanine
49. 2-fluoro-D-phenylalanine
50. 4-fluoro-L-phenylalanine
51. 4-fluoro-D-phenylalanine
52. 3-fluoro-DL-tyrosine
53. L-homophenylalanine
54. D-homophenylalanine
55. 2-hydroxy-3-methyl-L-phenylalanine
56. 2-hydroxy-3-methyl-D-phenylalanine
57. 2-hydroxy-3-methyl-DL-phenylalanine
58. 2-hydroxy-4-methyl-L-phenylalanine
59. 2-hydroxy-4-methyl-D-phenylalanine
60. 2-hydroxy-4-methyl-DL-phenylalanine
61. 2-hydroxy-5-methyl-L-phenylalanine
62. 2-hydroxy-5-methyl-D-phenylalanine
63. 2-hydroxy-5-methyl-DL-phenylalanine
64. β-hydroxy-DL-phenylalanine (DL-threo-3-phenyl serine)
65. 7-hydroxy-(S)-1,2,3,4-tetrahydroisoquinoline-3-carboxylic acid (hydroxy-Tic-OH)
66. 7-hydroxy-(R)-1,2,3,4-tetrahydroisoquinoline-3-carboxylic acid (hydroxy-D-Tic-OH)
67. 4-iodo-L-phenylalanine
68. 4-iodo-D-phenylalanine
69. 3-iodo-L-tyrosine
70. α-methyl-3-methoxy-DL-phenylalanine
71. α-methyl-4-methoxy-L-phenylalanine
72. α-methyl-4-methoxy-DL-phenylalanine
73. α-methyl-L-phenylalanine
74. α-methyl-D-phenylalanine
75. β-methyl-DL-phenylalanine
76. α-methyl-DL-tyrosine
77. O-methyl-L-tyrosine
78. O-methyl-D-tyrosine
79. 4-nitro-L-phenylalanine
80. 4-nitro-D-phenylalanine
81. 3-nitro-L-tyrosine
82. (S)-1,2,3,4-tetrahydroisoquinoline-3-carboxylic acid (L-Tic-OH)
83. (R)-1,2,3,4-tetrahydroisoquinoline-3-carboxylic acid (D-Tic-OH)
84. L-thyronine
85. DL-thyronine
86. L-thyroxine
87. D-thyroxine
88. 2,4,5-trihydroxy-DL-phenylalanine
89. 3,5,3'-triiodo-L-thyronine
90. DL-m-tyrosine
91. DL-o-tyrosine
92. 2-(trifluoromethyl)-L-phenylalanine
93. 2-(trifluoromethyl)-D-phenylalanine
94. 2-cyano-L-phenylalanine
95. 2-cyano-D-phenylalanine
96. 2-methyl-L-phenylalanine
97. 2-methyl-D-phenylalanine
98. 3-(trifluoromethyl)-L-phenylalanine
99. 3-(trifluoromethyl)-D-phenylalanine
100. 3-cyano-L-phenylalanine
101. 3-cyano-D-phenylalanine
102. 3-fluoro-L-phenylalanine
103. fluoro-D-phenylalanine
104. 3-methyl-L-phenylalanine
105. 3-methyl-D-phenylalanine
106. 4-benzoyl-L-phenylalanine
107. 4-benzoyl-D-phenylalanine
108. 4-(trifluoromethyl)-L-phenylalanine
109. 4-(trifluoromethyl)-D-phenylalanine
110. 4-cyano-L-phenylalanine
111. 4-cyano-D-phenylalanine
112. 4-methyl-L-phenylalanine
113. 4-methyl-D-phenylalanine
114. 2,4-dichloro-L-phenylalanine
115. 2,4-dichloro-D-phenylalanine
116. 3,5-diiodo-L-tyrosine OSu
117. Exemplary conservative variants of arginine and lysine
118. L-2-amino-3-guanidinopropionic acid
119. L-2-amino-3-ureidopropionic acid (Albizziin)
120. L-citrulline
121. DL-citrulline
122. 2,6-diaminoheptanedioic acid (mixture of isomers)
123. N-ω,ω-dimethyl-L-arginine (symmetrical)
124. N-ε,ε-dimethyl-L-lysine hydrochloride salt
125. α-methyl-DL-ornithine
126. N-ω-nitro-L-arginine
127. N-ω-nitro-D-arginine
128. N-δ-benzyloxycarbonyl-L-ornithine
129. (N-δ-)-L-ornithine
130. (N-δ-)-D-ornithine
131. (N-δ-1-(4,4-dimethyl-2,6-dioxocyclohex-1-ylidene)ethyl)-D-ornithine (D-Orn-(Dde)-OH)
132. L-ornithine (Orn( )-OH)
133. (N-d-4-methyltrityl)-L-ornithine (Orn(Mtt)-OH)
134. (N-d-4-methyltrityl)-D-ornithine (D-Orn(Mtt)-OH)
135. Exemplary conservative variants of proline
136. cis-4-amino-L-proline methyl ester hydrochloride salt
137. trans-4-amino-L-proline methyl ester hydrochloride salt
138. (S)-azetidine-2-carboxylic acid
139. trans-4-cyano-L-proline
140. cis-4-cyano-L-proline methyl ester
141. trans-4-cyano-L-proline methyl ester
142. 3,4-dehydro-L-proline
143. (R)-5,5-dimethylthiazolidine-4-carboxylic acid
144. (4S,2RS)-2-ethylthiazolidine-4-carboxylic acid
145. trans-4-fluoro-L-proline
146. (2S,3S)-3-hydroxypyrrolidine-2-carboxylic acid (trans-3-hydroxy-L-proline)
147. (2S,4S)-(−)-4-hydroxypyrrolidine-2-carboxylic acid (cis-4-hydroxy-L-proline)
148. (2S,4R)-(−)-4-hydroxypyrrolidine-2-carboxylic acid (trans-4-hydroxy-L-proline)
149. (2R,4R)-(+)-4-hydroxypyrrolidine-2-carboxylic acid (cis-4-hydroxy-D-proline)

150. (2S,4R)-(−)-4-t-butoxypyrrolidine-2-carboxylic acid (trans-4-t-butoxy-L-proline)
151. (2S,5RS)-5-methylpyrrolidine-2-carboxylic acid
152. (4S,2RS)-2-methylthiazolidine-4-carboxylic acid
153. (2S,3R)-3-phenylpyrrolidine-2-carboxylic acid
154. (4S,2RS)-2-phenylthiazolidine-4-carboxylic acid
155. (S)-thiazolidine-2-carboxylic acid
156. (R)-thiazolidine-2-carboxylic acid
157. (S)-thiazolidine-4-carboxylic acid
158. (R)-thiazolidine-4-carboxylic acid (L-thioproline)
159. α-allyl-DL-proline
160. α-benzyl-DL-proline
161. α-(2-bromobenzyl)-DL-proline
162. α-(4-bromobenzyl)-DL-proline
163. α-(2-chlorobenzyl)-DL-proline
164. α-(3-chlorobenzyl)-DL-proline
165. α-(diphenylmethyl)-DL-proline
166. α-(4-fluorobenzyl)-DL-proline
167. α-methyl-DL-proline
168. α-(4-methylbenzyl)-DL-proline
169. α-(1-naphthylmethyl)-DL-proline
170. α-propyl-DL-proline
171. 4-benzyl-L-pyroglutamic
172. 4-(2-bromobenzyl)-L-pyroglutamic acid benzyl ester
173. 4-(4-bromobenzyl)-L-pyroglutamic acid benzyl ester
174. 4-(4-methylbenzyl)-L-pyroglutamic acid benzyl ester
175. Miscellaneous Hetercyclic Amino Acids
176. α-amino-3-chloro-4,5-dihydro-5-isoxazoleacetic acid
177. 2-amino-α-(methoxyimino)-4-thiazoleacetic acid (predominantly syn)
178. 5-aminoorotic acid
179. 2-aminopyridyl-3-carboxylic acid (2-aminonicotinic acid)
180. 6-aminopyridyl-3-carboxylic acid (6-aminonicotinic acid)
181. 2-aminothiazole-4-acetic acid
182. (S)-azetidine-2-carboxylic acid
183. azetidine-3-carboxylic acid
184. 4-carboxymethylpiperazine
185. 4-carboxymethylpiperazine
186. 2-carboxypiperazine
187. 3-carboxypiperidine
188. indoline-2-carboxylic acid
189. L-mimosine
190. 4-phenylpiperidine-4-carboxylic acid
191. (S)-(−)-piperidine-2-carboxylic acid (L-(−)-pipecolic acid)
192. (R)-(+)-piperidine-2-carboxylic acid (D-(+)-pipecolic acid)
193. (RS)-piperidine-2-carboxylic acid (DL-pipecolic acid)
194. piperidine-4-carboxylic acid (isonipecotic acid)
195. Exemplary conservative variants of alanine, glycine, valine, and leucine
196. 3-(2-furyl)-D-Ala-OH
197. 3-cyclopentyl-DL-Ala-OH
198. 3-(4-quinolyl)-DL-Ala-OH
199. 3-(4-quinolyl)-DL-Ala-OH dihydrochloride dihydrate
200. 3-(2-quinolyl)-DL-Ala-OH
201. 3-(2-quinoxalyl)-DL-Ala-OH
202. α-allyl-L-alanine
203. L-allylglycine
204. L-allylglycine dicyclohexylammonium salt
205. D-allylglycine
206. D-allylglycine dicyclohexylammonium salt
207. L-α-aminobutyric acid (Abu-OH)
208. D-α-aminobutyric acid (D-Abu-OH)
209. DL-β-aminobutyric acid (DL-β-Abu-OH)
210. γ-aminobutyric acid (γ-Abu-OH)
211. α-aminoisobutyric acid (Aib-OH)
212. DL-β-aminoisobutyric acid (DL-β-Aib-OH)
213. Di-N-α-aminomethyl-L-alanine
214. 2-amino-4,4,4-trifluorobutyric acid
215. 3-amino-4,4,4-trifluorobutyric acid
216. β-(3-benzothienyl)-L-alanine
217. β-(3-benzothienyl)-D-alanine
218. t-butyl-L-alanine
219. t-butyl-D-alanine
220. L-t-butylglycine
221. D-t-butylglycine
222. β-cyano-L-alanine
223. β-cyclohexyl-L-alanine (Cha-OH)
224. β-cyclohexyl-D-alanine (D-Cha-OH)
225. L-cyclohexylglycine (Chg-OH)
226. D-cyclohexylglycine (D-Chg-OH)
227. β-cyclopentyl-DL-alanine
228. β-cyclopenten-1-yl-DL-alanine
229. β-cyclopropyl-L-alanine
230. cyclopropyl-DL-phenylglycine
231. DL-dehydroarmentomycin
232. 4,5-dehydro-L-leucine
233. L-α,γ-diaminobutyric acid (Dab-OH)
234. D-α,γ-diaminobutyric acid (D-Dab-OH)
235. Di-L-α,γ-diaminobutyric acid (Dab( )-OH)
236. Di-D-α,γ-diaminobutyric acid (D-Dab( )-OH)
237. (N-γ-allyloxycarbonyl)-L-α,γ-diaminobutyric acid (Dab(Aloc)-OH)
238. (N-γ-)-L-α,γ-diaminobutyric acid (Dab( )-OH)
239. (N-γ-1-(4,4-dimethyl-2,6-dioxocyclohex-1-ylidene)ethyl)-L-α,γ-diaminobutyric acid (Dab(Dde)-OH)
240. (N-γ-4-methyltrityl)-L-α,γ-diaminobutyric acid (Dab(Mtt)-OH)
241. (N-γ-)-D-α,γ-diaminobutyric acid (D-Dab( )-OH)
242. (N-γ-1-(4,4-dimethyl-2,6-dioxocyclohex-1-ylidene)ethyl)-D-α,γ-diaminobutyric acid (D-Dab(Dde)-OH)
243. (N-γ-4-methyltrityl)-D-α,γ-diaminobutyric acid (D-Dab(Mtt)-OH)
244. L-α,β-diaminopropionic acid (Dap-OH)
245. D-α,β-diaminopropionic acid (D-Dap-OH)
246. Di-L-α,β-diaminopropionic acid (Dap( )-OH)
247. Di-D-α,β-diaminopropionic acid (D-Dap( )-OH)
248. (N-β-allyloxycarbonyl)-L-α,β-diaminopropionic acid (Dap(Aloc)-OH)
249. (N-β-)-L-α,β-diaminopropionic acid (Dap( )-OH)
250. β-(1-naphthyl)-D-alanine (D-1-Nal-OH)
251. β-(2-naphthyl)-L-alanine (2-Nal-OH)
252. β-(2-naphthyl)-D-alanine (D-2-Nal-OH)
253. L-phenylglycine (Phg-OH)
254. D-phenylglycine (D-Phg-OH)
255. L-propargylglycine
256. L-propargylglycine dicyclohexylammonium salt
257. D-propargylglycine
258. D-propargylglycine dicyclohexylammonium salt
259. β-(2-pyridyl)-L-alanine (L-2-pyridylalanine)
260. β-(2-pyridyl)-D-alanine (D-2-pyridylalanine)
261. β-(3-pyridyl)-L-alanine (L-3-pyridylalanine)
262. β-(3-pyridyl)-D-alanine (D-3-pyridylalanine)
263. β-(4-pyridyl)-L-alanine (L-4-pyridylalanine)
264. β-(4-pyridyl)-D-alanine (D-4-pyridylalanine)
265. β-(2-thienyl)-L-alanine (Thi-OH)
266. β-(2-thienyl)-D-alanine (D-Thi-OH)
267. L-(2-thienyl)glycine
268. D-(2-thienyl)glycine
269. L-(3-thienyl)glycine
270. D-(3-thienyl)glycine 271. 5,5,5-trifluoro-DL-leucine
272. 4,4,4-trifluoro-DL-valine
273. L-2-amino-3-(dimethylamino)propionic acid (aza-L-leucine)
274. DL-2-amino-3-(dimethylamino)propionic acid (aza-DL-leucine)
275. (N-β-1-(4,4-dimethyl-2,6-dioxocyclohex-1-ylidene)ethyl)-L-α,β-diaminopropionic acid (Dap(Dde)-OH)
276. (N-β-(2,4-dinitrophenyl))-L-α,β-diaminopropionic acid (Dap(Dnp)-OH)
277. (N-β-4-methyltrityl)-L-α,β-diaminopropionic acid (Dap(Mtt)-OH)
278. (N-β-)-L-α,β-diaminopropionic acid (Dap( )-OH)
279. (N-β-)-D-α,β-diaminopropionic acid (D-Dap( )-OH)
280. (N-β-1-(4,4-dimethyl-2,6-dioxocyclohex-1-ylidene)ethyl)-D-α,β-diaminopropionic acid (D-Dap(Dde)-OH)
281. 2,5-dihydro-D-phenylglycine
282. 2,4-dinitro-DL-phenylglycine
283. 2-fluoro-DL-phenylglycine
284. 4-fluoro-L-phenylglycine
285. 4-fluoro-D-phenylglycine
286. 3-fluoro-DL-valine
287. 4-hydroxy-D-phenylglycine
288. α-methyl-DL-leucine
289. β-(1-naphthyl)-L-alanine (1-Nal-OH)
290. β-(1-naphthyl)-D-alanine (D-1-Nal-OH)
291. Exemplary conservative variants of benzoic acid
292. 2-amino-4-fluorobenzoic acid
293. 2-amino-5-fluorobenzoic acid
294. 2-amino-6-fluorobenzoic acid
295. 2-amino-5-iodobenzoic acid
296. 2-amino-3-methoxybenzoic acid
297. 2-amino-5-methoxybenzoic acid
298. 3-amino-4-methoxybenzoic acid
299. 4-amino-3-methoxybenzoic acid
300. 2-amino-3-methylbenzoic acid
301. 2-amino-5-methylbenzoic acid
302. 2-amino-6-methylbenzoic acid
303. 3-amino-2-methylbenzoic acid
304. 3-amino-4-methylbenzoic acid
305. 4-amino-3-methylbenzoic acid
306. 3-aminomethylbenzoic acid (Mamb-OH)
307. 4-aminomethylbenzoic acid (Pamb-OH)
308. 2-amino-3,4,5-trimethoxybenzoic acid
309. Di-3,4-diaminobenzoic acid
310. Di-3,5-diaminobenzoic acid
311. 4-methylaminobenzoic acid
312. 5-acetamido-2-aminobenzoic acid (5-acetamidoanthranilic acid)
313. 2-aminobenzene-1,4-dicarboxylic acid
314. 3-aminobenzene-1,2-dicarboxylic acid
315. 2-aminobenzoic acid (2-Abz-OH)
316. 3-aminobenzoic acid (3-Abz-OH)
317. 4-aminobenzoic acid (4-Abz-OH)
318. 2-(2-aminobenzoyl)benzoic acid
319. 2-amino-5-bromobenzoic acid
320. 2-amino-4-chlorobenzoic acid
321. 2-amino-5-chlorobenzoic acid
322. 2-amino-6-chlorobenzoic acid
323. 3-amino-4-chlorobenzoic acid
324. 4-amino-2-chlorobenzoic acid
325. 5-amino-2-chlorobenzoic acid
326. 2-amino-4,5-dimethoxybenzoic acid
327. 2-amino-3,5-dimethylbenzoic acid
328. 2-amino-4-fluorobenzoic acid
329. Miscellaneous Aromatic Amino Acids
330. Di-2-amino-3-(2-aminobenzoyl)propionic acid
331. 4-aminocinnamic acid (predominantly trans)
332. 4-aminohippuric acid
333. 3-amino-2-naphthoic acid
334. 4-aminooxanilic acid
335. (3-aminophenyl)acetic acid
336. (4-aminophenyl)acetic acid
337. 4-(4-aminophenyl)butanoic acid
338. 3-amino-3-phenylpropionic acid
339. (4-aminophenylthio)acetic acid
340. (2R,3S)-2-amino-3-(phenylthio)butanoic acid
341. Analogs of Cysteine and Methionine
342. S-acetamidomethyl-L-penicillamine
343. S-acetamidomethyl-D-penicillamine
344. S-(2-aminoethyl)-L-cysteine
345. S-benzyl-L-cysteine
346. S-benzyl-D-cysteine
347. S-benzyl-DL-homocysteine
348. L-buthionine
349. L-buthioninesulfoximine
350. DL-buthioninesulfoximine
351. S-n-butyl-L-cysteine
352. S-t-butyl-L-cysteine
353. S-t-butyl-D-cysteine
354. S-carbamoyl-L-cysteine
355. S-carboxyethyl-L-cysteine
356. S-carboxymethyl-L-cysteine
357. L-cysteic acid
358. S-diphenylmethyl-L-cysteine
359. L-ethionine (2-amino-4-(ethyl(thio)butyric acid)
360. D-ethionine (D-2-amino-4-(ethyl(thio)butyric acid)
361. S-ethyl-L-cysteine
362. S-trityl-L-homocysteine
363. Di-L-homocystine
364. DL-methionine methylsulfonium chloride
365. S-4-methoxybenzyl-L-penicillamine
366. S-4-methoxybenzyl-L-penicillamine (Pen(4-MeOBzl)-OH)
367. S-4-methylbenzyl-L-penicillamine dicyclohexylammonium salt (Pen(4-MeBzl)-OH.DCHA)
368. S-methyl-L-cysteine
369. α-methyl-DL-methionine
370. S-(2-(4-pyridyl)ethyl)-L-cysteine
371. S-(2-(4-pyridyl)ethyl)-DL-penicillamine
372. Di-seleno-L-cystine
373. L-selenomethionine
374. DL-selenomethionine
375. S-trityl-L-penicillamine
376. S-trityl-D-penicillamine
377. Di-L-cystathion
378. Di-DL-cystathionine
379. Exemplary conservative variants of serine, threonine, and statine
380. 2-amino-3-methoxypropionic acid
381. L-α-methylserine
382. D-α-methylserine
383. (S)-2-amino-4-trityloxybutanoic acid (Hse(Trt)-OH)
384. (RS)-2-amino-4-trityloxybutanoic acid (DL-Hse(Trt)-OH)
385. (S)-2-amino-3-benzyloxypropionic acid
386. (R)-2-amino-3-benzyloxypropionic acid
387. (2S,3S)-2-amino-3-ethoxybutanoic acid
388. 2-amino-3-ethoxybutanoic acid
389. 2-amino-3-ethoxypropionic acid
390. 4-amino-3-hydroxybutanoic acid
391. (R)-2-amino-3-hydroxy-3-methylbutanoic acid
392. (S)-2-amino-3-hydroxy-3-methylbutanoic acid
393. (RS)-2-amino-3-hydroxy-3-methylbutanoic acid 394. (3S,4S)-4-amino-3-hydroxy-6-methylheptanoic acid (Sta-OH)
395. (2R,3R)-3-amino-2-hydroxy-5-methylhexanoic acid
396. (2R,3S)-3-amino-2-hydroxy-5-methylhexanoic acid
397. (2S,3R)-3-amino-2-hydroxy-5-methylhexanoic acid
398. (2S,3S)-3-amino-2-hydroxy-5-methylhexanoic acid
399. (2S,3R)-2-amino-3-hydroxy-4-methylpentanoic acid
400. (2R,3S)-2-amino-3-hydroxy-4-methylpentanoic acid
401. (2S,3RS)-2-amino-3-hydroxy-4-methylpentanoic acid
402. 2-amino-3-hydroxypentanoic acid
403. (2S,3R)-3-amino-2-hydroxy-4-phenylbutanoic acid
404. (2R,3R)-3-amino-2-hydroxy-4-phenylbutanoic acid
405. (2S,3S)-2-amino-3-methoxybutanoic acid
406. 2-amino-3-methoxybutanoic acid
407. (S)-2-amino-3-methoxypropionic acid
408. Miscellaneous Aliphatic Amino Acids
409. α-amino-1-adamantanepropionic acid
410. 2-aminobicyclo[2.2.1]heptane-2-carboxylic acid (mixture of isomers)
411. 3-endo-aminobicyclo[2.2.1]heptane-2-endo-carboxylic acid
412. 3-endo-aminobicyclo[2.2.1]heptane-2-endo-carboxylic acid
413. 3-endo-aminobicyclo[2.2.1]hept-5-ene-2-endo-carboxylic acid
414. 1-aminocyclobutane-1-carboxylic acid
415. 5-amino-1,3-cyclohexadiene-1-carboxylic acid
416. 1-aminocyclohexane-1-carboxylic acid
417. (±)-cis-2-aminocyclohexane-1-carboxylic acid
418. (±)-trans-2-aminocyclohexane-1-carboxylic acid
419. trans-4-aminocyclohexane-1-carboxylic acid
420. (±)-cis-3-aminocyclohexane-1-carboxylic acid
421. cis-4-aminocyclohexane-1-carboxylic acid
422. (±)-cis-2-aminocyclohex-4-ene-1-carboxylic acid
423. (±)-trans-2-aminocyclohex-4-ene-1-carboxylic acid
424. cis-4-aminocyclohexane-1-acetic acid
425. 1-aminocyclopentane-1-carboxylic acid
426. (±)-cis-2-aminocyclopentane-1-carboxylic acid
427. 1-aminocyclopropane-1-carboxylic acid
428. 2-aminoheptanoic acid
429. 7-aminoheptanoic acid
430. 6-aminohexanoic acid (6-aminocaproic acid)
431. 5-aminolevulinic acid
432. trans-4-(aminomethyl)cyclohexane-1-carboxylic acid
433. 2-aminooctanoic acid
434. 8-aminooctanoic acid (8-Aminocaprylic acid)
435. 3-(aminooxy)acetic acid
436. 5-aminopentanoic acid
437. 11-aminoundecanoic acid
438. β-Amino Acids
439. β-alanine (β-Ala-OH)
440. L-β-homoalanine (β-homoAla-OH)
441. (S)—N-ω-2,2,4,6,7-pentamethyldihydrobenzofuran-5-sulfonyl-L-β-homoarginine (β-homoArg(Pbf)-OH)
442. N-ω-tosyl-L-β-homoarginine (β-homoArg(Tos)-OH)
443. γ-trityl-L-β-homoasparagine (β-homoAsn(Trt)-OH)
444. L-β-homoaspartic acid γ-t-butyl ester (β-homoAsp(OtBu)-OH)
445. L-β-homoaspartic acid γ-benzyl ester (β-homoAsp(OBzl)-OH)
446. L-β-homoglutamic acid δ-t-butyl ester (β-homoGlu(OtBu)-OH)
447. L-β-homoglutamic acid δ-benzyl ester (β-homoGlu(OBzl)-OH)
448. N-δ-trityl-L-β-homoglutamine (β-homoGln(Trt)-OH)
449. O-t-butyl-L-β-homohydroxyproline (β-homoHyp(tBu)-OH)
450. L-β-homoisoleucine (β-homoIle-OH)
451. DL-β-leucine (DL-β-Leu-OH)
452. L-β-homoleucine (β-homoLeu-OH)
453. L-N-ω-β-homolysine (β-homoLys( )-OH)
454. L-N-ω-2-benzyloxycarbonyl-β-homolysine (β-homoLys(Z)—OH)
455. L-β-homomethionine (β-homoMet-OH)
456. L-β-phenylalanine (β-Phe-OH)
457. D-β-phenylalanine (D-β-Phe-OH)
458. L-β-homophenylalanine (β-homoPhe-OH)
459. L-β-homoproline (β-homoPro-OH)
460. O-t-butyl-L-β-homoserine (β-homoSer(tBu)-OH)
461. O-benzyl-L-β-homoserine (β-homoSer(Bzl)-OH)
462. O-benzyl-L-β-homothreonine (β-homoThr(Bzl)-OH)
463. L-β-homotryptophan (β-homoTrp-OH)
464. O-t-butyl-L-β-homotyrosine (β-homoTyr(tBu)-OH)
465. L-β-homovaline (β-homoVal-OH)
466. (R)-3-amino-4-(3-benzothienyl)butyric acid
467. (S)-3-amino-4-(3-benzothienyl)butyric acid
468. 3-aminobicyclo[2.2.2]octane-2-carboxylic acid (mixture of isomers)
469. (R)-3-amino-4-(4-bromophenyl)butyric acid
470. (S)-3-amino-4-(4-bromophenyl)butyric acid
471. (R)-3-amino-4-(2-chlorophenyl)butyric acid
472. (S)-3-amino-4-(2-chlorophenyl)butyric acid
473. (R)-3-amino-4-(3-chlorophenyl)butyric acid
474. (S)-3-amino-4-(3-chlorophenyl)butyric acid
475. (R)-3-amino-4-(4-chlorophenyl)butyric acid
476. (S)-3-amino-4-(4-chlorophenyl)butyric acid
477. 3-amino-3-(4-chlorophenyl)propionic acid
478. (R)-3-amino-4-(2-cyanophenyl)butyric acid
479. (S)-3-amino-4-(2-cyanophenyl)butyric acid
480. (R)-3-amino-4-(3-cyanophenyl)butyric acid
481. (S)-3-amino-4-(3-cyanophenyl)butyric acid
482. (R)-3-amino-4-(4-cyanophenyl)butyric acid
483. (S)-3-amino-4-(4-cyanophenyl)butyric acid
484. (R)-3-amino-4-(2,4-dichlorophenyl)butyric acid
485. (S)-3-amino-4-(2,4-dichlorophenyl)butyric acid
486. (R)-3-amino-4-(3,4-dichlorophenyl)butyric acid
487. (S)-3-amino-4-(3,4-dichlorophenyl)butyric acid
488. (R)-3-amino-4-(3,4-difluorophenyl)butyric acid
489. (S)-3-amino-4-(3,4-difluorophenyl)butyric acid
490. (R)-3-amino-4-(2-fluorophenyl)butyric acid
491. (S)-3-amino-4-(2-fluorophenyl)butyric acid
492. (R)-3-amino-4-(3-fluorophenyl)butyric acid
493. (S)-3-amino-4-(3-fluorophenyl)butyric acid
494. (R)-3-amino-4-(4-fluorophenyl)butyric acid
495. (S)-3-amino-4-(4-fluorophenyl)butyric acid
496. (R)-3-amino-4-(2-furyl)butyric acid
497. (S)-3-amino-4-(2-furyl)butyric acid
498. (R)-3-amino-5-hexenoic acid
499. (S)-3-amino-5-hexenoic acid
500. (R)-3-amino-5-hexynoic acid
501. (S)-3-amino-5-hexynoic acid
502. (R)-3-amino-4-(4-iodophenyl)butyric acid
503. (S)-3-amino-4-(4-iodophenyl)butyric acid
504. (R)-3-amino-4-(2-methylphenyl)butyric acid
505. (S)-3-amino-4-(2-methylphenyl)butyric acid
506. (R)-3-amino-4-(3-methylphenyl)butyric acid
507. (S)-3-amino-4-(3-methylphenyl)butyric acid
508. (R)-3-amino-4-(4-methylphenyl)butyric acid
509. (S)-3-amino-4-(4-methylphenyl)butyric acid
510. (R)-3-amino-4-(1-naphthyl)butyric acid
511. (S)-3-amino-4-(1-naphthyl)butyric acid
512. (R)-3-amino-4-(2-naphthyl)butyric acid
513. (S)-3-amino-4-(2-naphthyl)butyric acid
514. (R)-3-amino-4-(4-nitrophenyl)butyric acid 515. (S)-3-amino-4-(4-nitrophenyl)butyric acid
516. (R)-3-amino-4-pentafluorophenylbutyric acid
517. (S)-3-amino-4-pentafluorophenylbutyric acid
518. (R)-3-amino-6-phenyl-5-hexenoic acid
519. (S)-3-amino-6-phenyl-5-hexenoic acid
520. (R)-3-amino-5-phenylpentanoic acid
521. (S)-3-amino-5-phenylpentanoic acid
522. (R)-3-amino-4-(3-pyridyl)butyric acid
523. (S)-3-amino-4-(3-pyridyl)butyric acid
524. (R)-3-amino-4-(4-pyridyl)butyric acid
525. (S)-3-amino-4-(4-pyridyl)butyric acid
526. (R)-3-amino-4-(2-thienyl)butyric acid
527. (S)-3-amino-4-(2-thienyl)butyric acid
528. (R)-3-amino-4-(3-thienyl)butyric acid
529. (S)-3-amino-4-(3-thienyl)butyric acid
530. 3-amino-3-(2-thienyl)propionic acid
531. 3-amino-4,4,4-trifluorobutyric acid
532. (R)-3-amino-4-(2-trifluoromethylphenyl)butyric acid
533. (S)-3-amino-4-(2-trifluoromethylphenyl)butyric acid
534. (R)-3-amino-4-(3-trifluoromethylphenyl)butyric acid
535. (S)-3-amino-4-(3-trifluoromethylphenyl)butyric acid
536. (R)-3-amino-4-(4-trifluoromethylphenyl)butyric acid
537. (S)-3-amino-4-(4-trifluoromethylphenyl)butyric acid
538. (R)-1,2,3,4-tetrahydroisoquinoline-3-acetic acid
539. (S)-1,2,3,4-tetrahydroisoquinoline-3-acetic acid
540. 1,2,5,6-tetrahydropyridine-3-carboxylic acid (guvacine)
541. H-L-β-Homopro-OH HCl (S)-2-(2-Pyrrolidinyl) acetic acid hydrochloride
542. H-DL-β-Leu-OH (1)-3-Amino-4-methylpentanoic acid
543. H-DL-β-Homoleu-OH (1)-3-Amino-5-methylcaproic acid
544. H-DL-β-Phe-OH (1)-3-Amino-3-phenylpropionic acid
545. L-Homophe-OEt HCl
546. D-Homophe-OEt HCl
547. N-Benzyl-L-Homophe-OEt HCl
548. N-Benzyl-D-Homophe-OEt HCl
549. (1)-3-(amino)-4-(4-biphenylyl)butyric acid
550. (1)-3-Amino-4-(4-biphenylyl)butyric acid hydrochloride
551. (+)-Ethyl (S)-2-amino-4-cyclohexylbutyrate hydrochloride
552. (−)-Ethyl (R)-2-amino-4-cyclohexylbutyrate hydrochloride
553. N-α-Methyl Amino Acids
554. N-α-methyl-L-alanine (MeAla-OH)
555. N-α-methyl-D-alanine (D-MeAla-OH)
556. N-α-methyl-L-alloisoleucine (MeAlloIle-OH)
557. N-α-methyl-D-alloisoleucine (D-MeAlloIle-OH)
558. N-α-methyl-N-ω-tosyl-L-arginine (MeArg(Tos)-OH)
559. N-α-methyl-N-ω-2,2,4,6,7-pentamethyldihydrobenzofuran-5-sulfonyl-D-arginine (D-MeArg(Pbf)-OH)
560. N-α-methyl-N-ω-tosyl-D-arginine (D-MeArg(Tos)-OH)
561. N-α-methyl-L-aspartic acid
562. N-α-methyl-L-aspartic acid β-t-butyl ester (MeAsp(OtBu)-OH)
563. N-α-methyl-D-aspartic acid
564. N-α-methyl-D-aspartic acid β-t-butyl ester (D-MeAsp(OtBu)-OH)
565. N-α-methyl-4-chloro-L-phenylalanine (Me(4-Cl-Phe)-OH)
566. N-α-methyl-4-chloro-D-phenylalanine (D-Me(4-Cl-Phe)-OH)
567. N-α-methyl-L-glutamic acid γ-t-butyl ester (MeGlu(OtBu)-OH)
568. N-α-methyl-D-glutamic acid γ-t-butyl ester (D-MeGlu(OtBu)-OH)
569. N-α-methylglycine (sarcosine; Sar-OH)
570. N-α-methyl-N-im-trityl-L-histidine (MeHis(Trt)-OH)
571. N-α-methyl-N-im-trityl-D-histidine (D-MeHis(Trt)-OH)
572. N-α-methyl-trans-L-4-hydroxyproline
573. N-α-methyl-L-isoleucine (MeIle-OH)
574. N-α-methyl-L-leucine (MeLeu-OH)
575. N-α-methyl-D-leucine (D-MeLeu-OH)
576. N-α-methyl-N-ε-t-L-lysine (MeLys( )-OH)
577. N-α-methyl-N-ε-2-chlorobenzyloxycarbonyl-L-lysine (MeLys(2-Cl—Z)—OH)
578. N-α-methyl-4-nitro-L-phenylalanine (MePhe(4-NO2)-OH)
579. N-α-methyl-L-norleucine (MeNle-OH)
580. N-α-methyl-L-norvaline (MeNva-OH)
581. N-α-methyl-L-phenylalanine (MePhe-OH)
582. N-α-methyl-D-phenylalanine (D-MePhe-OH)
583. N-α-methyl-L-phenylglycine (MePhg-OH)
584. N-α-methyl-L-proline
585. N-α-methyl-O-benzyl-L-serine (MeSer(Bzl)-OH)
586. N-α-methyl-O-benzyl-L-serine dicyclohexylammonium salt (MeSer(Bzl)-OH.DCHA)
587. N-α-methyl-O-t-butyl-L-serine (MeSer(tBu)-OH)
588. N-α-methyl-O-t-butyl-L-threonine (MeThr(tBu)-OH)
589. N-α-methyl-L-tryptophan (MeTrp-OH)
590. N-α-methyl-DL-tryptophan (DL-MeTrp-OH)
591. N-α-methyl-O-benzyl-L-tyrosine (MeTyr(Bzl)-OH)
592. N-α-methyl-O-t-butyl-L-tyrosine (MeTyr(tBu)-OH)
593. N-α-methyl-O-methyl-L-tyrosine (MeTyr(Me)-OH)
594. N-α-methyl-O-benzyl-D-tyrosine (D-MeTyr(Bzl)-OH)
595. N-α-methyl-L-valine (MeVal-OH)
596. N-α-methyl-D-valine (D-MeVal-OH)
597. Amino Alcohols
598. L-alaninol
599. D-alaninol
600. 2-aminobenzylalcohol
601. 3-aminobenzylalcohol
602. 4-aminobenzylalcohol
603. (R)-(−)-2-aminobutanol
604. (S)-(+)-2-aminobutanol
605. 4-aminobutanol
606. 4-amino-2-butanol
607. 2-amino-5-chlorobenzylalcohol
608. (±)-cis-2-aminocyclohexanol
609. (±)-trans-2-aminocyclohexanol
610. trans-4-aminocyclohexanol
611. (1R,2S)-(−)-2-amino-1,2-diphenylethanol
612. (1S,2R)-(+)-2-amino-1,2-diphenylethanol
613. 2-(2-aminoethoxy)ethanol
614. α-(1-aminoethyl)-4-hydroxybenzyl alcohol
615. 2-amino-2-ethyl-1,3-propanediol
616. 6-aminohexanol
617. 1-amino-4-(2-hydroxyethyl)piperazine
618. (1R,2S)-(+)-cis-1-amino-2-indanol
619. (1 S,2R)-(−)-cis-1-amino-2-indanol
620. (1 S,2R)-(+)-2-amino-3-methoxyphenylpropanol
621. (±)-cis-2-aminomethylcycloheptanol
622. (±)-1-aminomethylcyclohexanol
623. (±)-cis-2-aminomethylcyclohexanol
624. (±)-trans-2-aminomethylcyclohexanol
625. (±)-cis-2-aminomethylcyclooctanol
626. 6-amino-2-methyl-2-heptanol (heptaminol)
627. α-aminomethyl-3-hydroxybenzyl alcohol (norphenylephrine)

628. α-aminomethyl-4-hydroxybenzyl alcohol (octopamine)
629. α-aminomethyl-4-hydroxy-3-methoxybenzyl alcohol (normetaephrine)
630. 2-amino-2-methyl-1,3-propanediol
631. 2-amino-2-methylpropanol (β-aminoisobutanol)
632. (1R,2R)-(−)-2-amino-1-(4-nitrophenyl)-1,3-propanediol
633. (1S,2S)-(+)-2-amino-1-(4-nitrophenyl)-1,3-propanediol
634. 5-aminopentanol
635. 1-amino-3-phenoxy-2-propanol
636. (R)-(−)-2-amino-1-phenylethanol
637. (S)-(+)-2-amino-1-phenylethanol
638. 2-(4-aminophenyl)ethanol
639. (1R,2R)-(−)-2-amino-1-phenyl-1,3-propanediol
640. (1S,2S)-(+)-2-amino-1-phenyl-1,3-propanediol
641. 3-amino-3-phenylpropanol
642. (RS)-3-amino-1,2-propanediol
643. (S)-(+)-3-amino-1,2-propanediol
644. (R)-(−)-1-amino-2-propanol
645. (S)-(+)-1-amino-2-propanol
646. 3-amino-1-propanol
647. N-ω-2,2,4,6,7-pentamethyldihydrobenzofuran-5-sulfonyl-L-argininol (Arg(Pbf)-ol)
648. N-ω-tosyl-L-argininol
649. N-β-trityl-L-asparaginol (Asn(Trt)-ol)
650. L-asparaginol (Asn-ol)
651. N-β-trityl-D-asparaginol (D-Asn(Trt)-ol)
652. D-asparaginol (D-Asn-ol)
653. L-aspartimol β-t-butyl ester (Asp(OtBu)-ol)
654. D-aspartimol β-t-butyl ester (D-Asp(OtBu)-ol)
655. DL-4-chlorophenylalaninol
656. β-cyclohexyl-L-alaninol
657. S-t-butyl-L-cysteinol (Cys(tBu)-ol)
658. S-t-butyl-D-cysteinol (D-Cys(tBu)-ol)
659. 1,1-diphenyl-L-alaninol
660. L-glutaminol (Gln-ol)
661. N-γ-trityl-L-glutaminol (Gln(Trt)-ol)
662. L-glutamol γ-t-butyl ester (Glu(OtBu)-ol)
663. L-glutamol γ-benzyl ester (Glu(OBzl)-ol)
664. D-glutamol γ-t-butyl ester (D-Glu(OtBu)-ol)
665. D-glutamol γ-benzyl ester (D-Glu(OtBu)-ol)
666. ethanolamine (Gly-ol)
667. N-im-t-L-histidinol
668. N-im-trityl-L-histidinol
669. N-im-benzyl-L-histidinol
670. 1-hydroxyethylethoxypiperazine
671. N-(2-hydroxyethyl)piperazine
672. N-(2-hydroxyethyl)-1,3-propanediamine
673. 3-endo-hydroxymethylbicyclo[2.2.1]hept-5-enyl-2-endo-amine
674. (±)-cis-2-hydroxymethyl-4-cyclohexenyl-1-amine
675. (±)-cis-2-hydroxymethyl-1-cyclohexylamine
676. (±)-trans-2-hydroxymethyl-1-cyclohexylamine
677. (±)-cis-2-hydroxymethyl-trans-4-phenyl-1-cyclohexylamine
678. 3-hydroxypiperidine
679. 4-hydroxypiperidine
680. L-isoleucinol (Ile-ol)
681. L-leucinol (leu-ol)
682. D-leucinol (D-leu-ol)
683. L-tert-leucinol ((S)-(−)-2-amino-3,3-dimethyl-1-butanol)
684. N-ε-t-L-lysinol (Lys( )-ol)
685. N-ε-benzyloxycarbonyl-L-lysinol (Lys(Z)-ol)
686. N-ε-2-cholorobenzyloxycarbonyl-L-lysinol (Lys(2-Cl—Z)-ol)
687. N-ε-t-D-lysinol (D-Lys( )-ol)
688. N-ε-benzyloxycarbonyl-D-lysinol (D-Lys(Z)-ol)
689. N-ε-2-cholorobenzyloxycarbonyl-D-lysinol (D-Lys(2-Cl—Z)-ol)
690. L-methioninol (Met-ol)
691. D-methioninol (D-Met-ol)
692. (1R,2S)-(−)-norephedrine
693. (1S,2R)-(+)-norephedrine
694. L-norleucinol
695. L-norvalinol
696. L-phenylalaninol
697. D-phenylalaninol (D-Phe-ol)
698. L-phenylglycinol (Phg-ol)
699. D-phenylglycinol (D-Phg-ol)
700. 2-(2-piperidyl)ethanol
701. 2-(4-piperidyl)ethanol
702. 2-piperidylmethanol
703. L-prolinol (Pro-ol)
704. D-prolinol (D-Pro-ol)
705. O-benzyl-L-serinol (Ser(Bzl)-ol)
706. O-t-butyl-L-serinol (Ser(tBu)-ol)
707. O-benzyl-D-serinol (D-Ser(Bzl)-ol)
708. O-t-butyl-D-serinol (D-Ser(tBu)-ol)
709. O-butyl-L-threoninol (Thr(tBu)-ol)
710. O-t-butyl-D-threoninol (Thr(tBu)-ol)
711. O-butyl-D-threoninol (Thr(tBu)-ol)
712. L-tryptophanol (Trp-ol)
713. D-tryptophanol (D-Trp-ol)
714. O-benzyl-L-tyrosinol (Tyr(Bzl)-ol)
715. O-t-butyl-L-tyrosinol (Tyr(tBu)-ol)
716. O-benzyl-D-tyrosinol (D-Tyr(Bzl)-ol)
717. L-valinol (Val-ol)
718. D-valinol (D-Val-ol)
719. Others
720. Norleucine
721. Ethionine
722. Ornithine
723. Thi-OH (−)-(R)-4-thiazolidine-carboxylic acid
724. 2-phosphonoglycine trimethyl ester
725. iminodiacetic acid
726. (1)-2-Aminoheptanedioic acid
727. (1)-2-Aminopimelic acid
728. 2-[2-(amino)ethoxy]ethoxy}acetic acid
729. 8-(amino)-3,6-dioxaoctanoic acid
730. 1-azetidine-3-carboxylic acid
731. (1R,4S)-(+)-4-(amino)-2-cyclopentene-1-carboxylic acid
732. cycloleucine
733. homocycloleucine
734. Freidinger's lactam
735. 1,2,3,4-tetrahydronorharman-3-carboxylic acid
736. 4-(aminomethyl)benzoic acid
737. 3-(aminomethyl)benzoic acid
738. 4-Abz-OH 4-(amino)benzoic acid
739. 3-Abz-OH 3-(amino)benzoic acid
740. 2-Abz-OH 2-(amino)benzoic acid
741. 2-(amino)isobutyric acid
742. 12-(amino)dodecanoic acid
743. 8-(amino)caprylic acid
744. 7-(amino)enanthic acid
745. 6-(amino)caproic acid
746. 5-(amino)pentanoic acid
747. 4-(amino)butyric acid
748. N'-diaminoacetic acid
749. L-2,3-diaminopropionic acid 750. N-β-L-2,3-diaminopropionic acid
751. (R)-4-(amino)-3-(Z-amino)butyric acid
752. (S)-4-(amino)-3-(Z-amino)butyric acid
753. 1,6-hexanediamine HCl
754. -1,5-pentanediamine
755. N-p-phenylenediamine
756. N-1,4-butanediamine
757. N-1,3-propanediamine
758. N-ethylenediamine
759. N—N-methylethylenediamine
760. 1-piperazine
761. 1-homopiperazine The peptide may be a L-enantiomer (comprising natural L-amino acids). The peptide may also be a D-enantiomer (comprising D-amino acids).

The peptide may comprise all L-amino acids. Alternatively, the peptide may comprise all D-amino acids. In some cases, the peptide may comprise a mixture of L- and D-amino acids. The peptide may comprise mainly L-amino acids but a small number of D-amino acids (for example up to 1, 2, 3, 4, 5 or 10 D-amino acids). Likewise, the peptide may comprise mainly D-amino acids but a small number of L-amino acids (e.g. up to 1, 2, 3, 4, 5 or 10 L-amino acids).

In particular, the peptide may be a D-enantiomer of SEQ ID NO: 14 (either comprising or consisting of the sequence, or a variant, as described above). Furthermore, the peptide may be a retro-peptide (L-amino acids in reverse order), or a retro-inverse peptide (D-amino acids in reverse order).

With regards to antimicrobial activity, the peptide may exhibit a minimum inhibitory concentration of 7 µM or less, preferably 6 µM or less, more preferably 5.5 µM or less for *E. coli, S. typhimurium, C. albicans, S. epidermidis, S. aureus* and *E. faecalis*. The minimum inhibitory concentration (MIC) is the lowest concentration of an antimicrobial that will inhibit the visible growth of a microorganism after overnight incubation. Methods for determining MIC values are well known in the art. Such methods include the modified broth microdilution method, with an inoculum of 2-7× $10^5$ bacteria per ml. Plates are incubated at 37° C. overnight (12-18 hours) and the concentration of peptide where no growth is observed is identified as the MIC.

The peptides may be tagged. For example, as shown in the Appendix below the peptides may e.g. have a -bA-bA-C tag (beta-alanine, beta-alanine, cysteine) or -BB-k (Biotin) tag (beta-alanine, beta-alanine, modified lysine with biotin attached to the side chain).

Methods for synthesising peptides are well known in the art, and include both solid-phase and liquid-phase synthesis. Peptides of the invention can be synthesized by such commonly used methods as t-Boc or Fmoc protection of alpha-amino groups. Both methods involve stepwise syntheses whereby a single amino acid is added at each step starting from the C terminus of the peptide (See, Coligan, et al., Current Protocols in Immunology, Wiley Interscience, 1991, Unit 9). Peptides of the invention can also be synthesized by the well known solid phase peptide synthesis methods described in Merrifield, J. Am. Chem. Soc., 85:2149, (1962), and Stewart and Young, Solid Phase Peptides Synthesis, (Freeman, San Francisco, 1969, pp. 27-62), using a copoly (styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The peptide is added to the culture medium at any appropriate concentration which enhances growth of the slow-growing Mycobacterial species. Optimum concentrations may be determined by measuring growth of a particular species in the presence of a variety of peptide concentrations. Typically, the peptide is present in the culture medium at a final concentration of at least 5 µg/ml, preferably at least 10 µg/ml. The peptide may be present at a final concentration of from 5 µg/ml to 200 µg/ml, preferably from 10 to 100 µg/ml. More preferably, the peptide is present at a final concentration of from 10 to 50 µg/ml. Most preferably, the peptide is present at a final concentration of from 20 µg/ml to 50 µg/ml.

In some cases, the peptide may though be present at a final concentration of from 5 µg/ml to 50 µg/ml or even from 5 µg/ml to 25 µg/ml.

Peptides may be provided already in the culture medium. As an alternative, the peptide may be provided separately to the culture medium, and supplemented into the culture medium prior to use. In this scenario, the peptide may be stored in solution or in dried form. When stored in dried form, the peptide may be rehydrated using an appropriate solvent before use.

In the method of the invention, the medium may comprise two or more cationic peptides. The cationic peptides may be any of those described above.

Use of Cationic Antimicrobial Peptides

The invention also provides for use of cationic antimicrobial peptides for enhancing growth of cells of a slow-growing Mycobacterial species. The peptides and Mycobacterial species/subspecies may be any of those described above.

Kit

The present invention also provides a kit comprising one or more antimicrobial peptides as described above and instructions for performing the method as described above. The kit may comprise an appropriate media comprising the peptide. The kit may also comprise the antimicrobial peptide in solution or in dried form. When present in dried form, the kit may comprise a solution for rehydration of the peptide.

The kit may additionally comprise one or more other reagents or instruments which enables the method to be carried out. For example, the kit may comprise an appropriate media.

Screening Method

The present invention also provides a screening method for identifying peptides which enhance growth of cells of a slow-growing Mycobacterial species. The method comprises culturing the cells of the slow-growing Mycobacterial species in a growth medium comprising the peptide and monitoring growth of the cells. The peptide is from 6 to 50 amino acids in length, includes one or more positively charged amino acids and comprises at least 20% hydrophobic residues. The peptide may have any of the features described above. The Mycobacterial species and growth medium may also be any of those described above.

The method then comprises providing an output which identifies the peptide as enhancing the growth of the cells.

The output may be recording information e.g. in a laboratory notebook. The output may also be information recorded on a computer.

The peptide is identified as enhancing growth of the cells if it results in a reduction in the lag phase and/or an increase in the division rate for a particular Mycobacterial species. As described above, the lag phase and the division rate may be determined from plotting the optical density of a culture against time. The results are typically compared to control values, either where a Mycobacterial culture is grown under the same conditions in the absence of any peptide supplement (negative control), or where the culture is grown in the presence of a peptide known to enhance growth of the Mycobacteria (positive control). The peptide known to enhance the growth of Mycobacteria may be any of those identified above.

A peptide is then identified as enhancing growth of the Mycobacteria (a) if it reduces the lag phase and/or enhances the division rate of the bacteria in comparison with the negative control, or (b) if it results in a similar or decreased lag time, or a similar or increased division rate, in comparison with the positive control. A skilled person could readily interpret the results and identify whether lag phases and division rates are similar, decreased, or increased.

The following Examples illustrate the invention.

EXAMPLES

Example 1

Using *Mycobacterium avium* subspecies *paratuberculosis* (MAP) as a target organism a bank of 109 short L enantiomer peptides and one D enantiomer peptide (TiKa 14D) were screened for the ability to supplement defined media (see below) to produce growth effects that produce biomass more rapidly than identical inocula of MAP with no added supplement.

The effects can be defined as:
A significant decrease in lag time (i.e the time it takes to recover from subculture and begin growing exponentially). With standard low inoculum this is at least 5 days but there is evidence that this phase can also be greatly extended in low inocula (see FIGS. 3 and 4).
An increase in division rate.

Results over a 20 day period are presented in FIG. 1 for a number of peptides (supplemented at a concentration of 20 mg/ml (final)). TiKa supplements (the antimicrobial peptides) shown to produce positive effects were 14D, 14L, 69, 86, 102 and 103 (see appendix). Some TiKa supplements increased the division rate more than 1.5 fold and in some cases more than 2 fold. All other Tika supplements (see appendix for sequences) did not produce a significantly positive effect on the test culture.

Example 2

Figure 2:
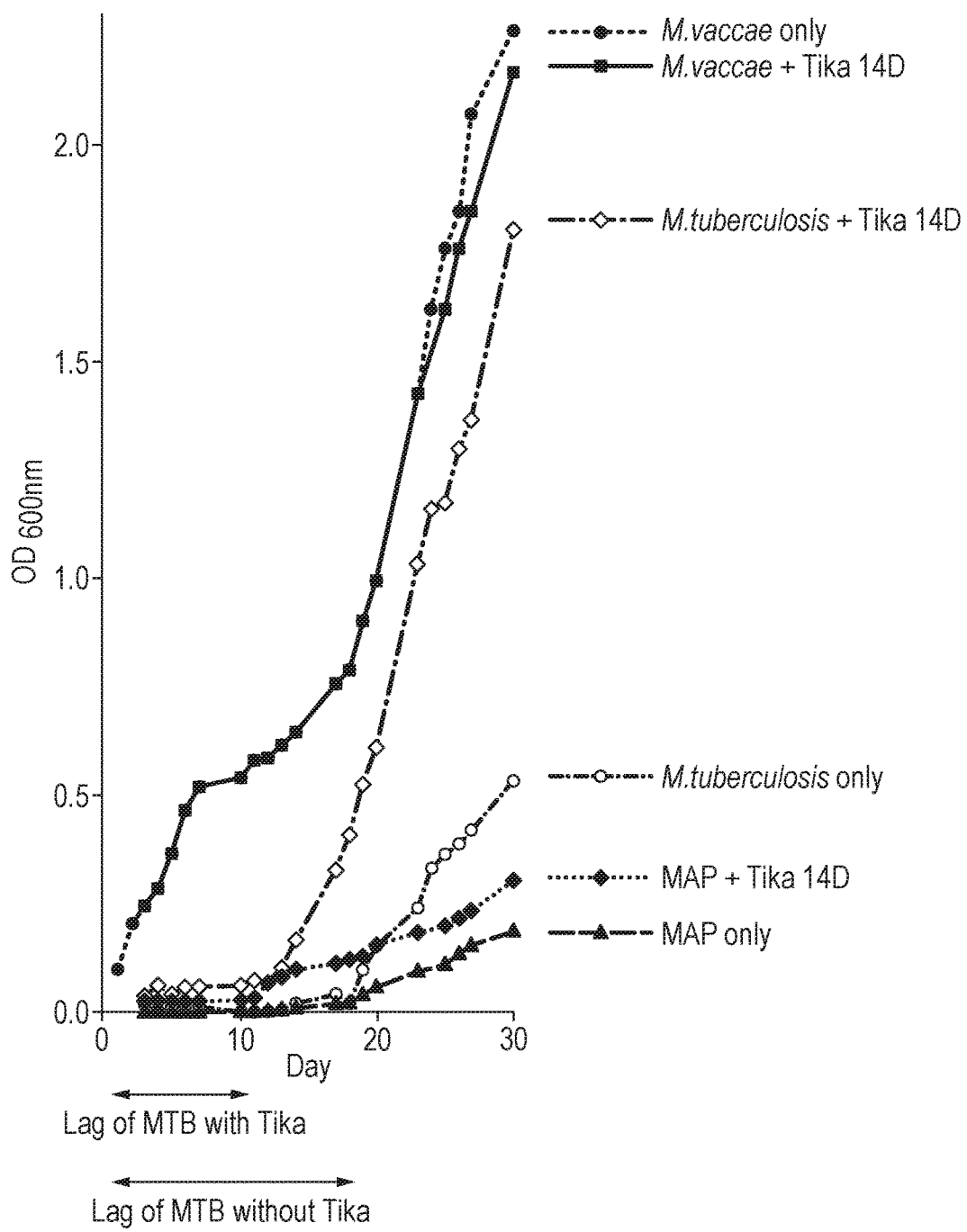
FIG. 2 shows growth curves of three Mycobacterial species (MAP, *M. tuberculosis* and *M. vaccae*) in the presence of TiKa 14D (20 μg/ml).

Activity of the TiKa peptides was tested for a number of Mycobacterial species and subspecies. FIG. 2 presents results for TiKa 14D (20 µg/ml) on *Mycobacterium tuberculosis*, *Mycobacterium avium* subspecies *paratuberculosis* and *Mycobacterium vaccae*. As shown in the Figure, TiKa 14D had positive effects on *Mycobacterium tuberculosis* and *Mycobacterium avium* subspecies *paratuberculosis*, but not on *Mycobacterium vaccae*.

Mycobacterial species shown to respond with positive effect in conventional media with TiKa added to an optimal concentration were:

*Mycobacterium avium* subspecies *paratuberculosis*;
*Mycobacterium avium* subspecies *silvaticum*;
*Mycobacterium avium* subspecies *hominissuis*;
*Mycobacterium avium* subspecies *avium*;
*Mycobacterium bovis* (including *Bacillus* Calmette Guerin); and
*Mycobacterium tuberculosis*.

Mycobacterial species with no observed effects, or with negative observed effects, with TiKa supplements added at 20 µg/ml were:

*Mycobacterium vaccae*;
*Mycobacterium smegmatis*;
*Mycobacterium celatum*;
*Mycobacterium kansasii*;
*Mycobacterium gordonae*;
*Mycobacterium porcinum*;
*Mycobacterium cheloni*; and
*Mycobacterium flavescens*.

Example 3

The effects of TiKa 14D on cultures with different starting $OD_{600}$ values were tested. The TiKa 14D was present at a concentration of 20 µg/ml.

Figure 3:
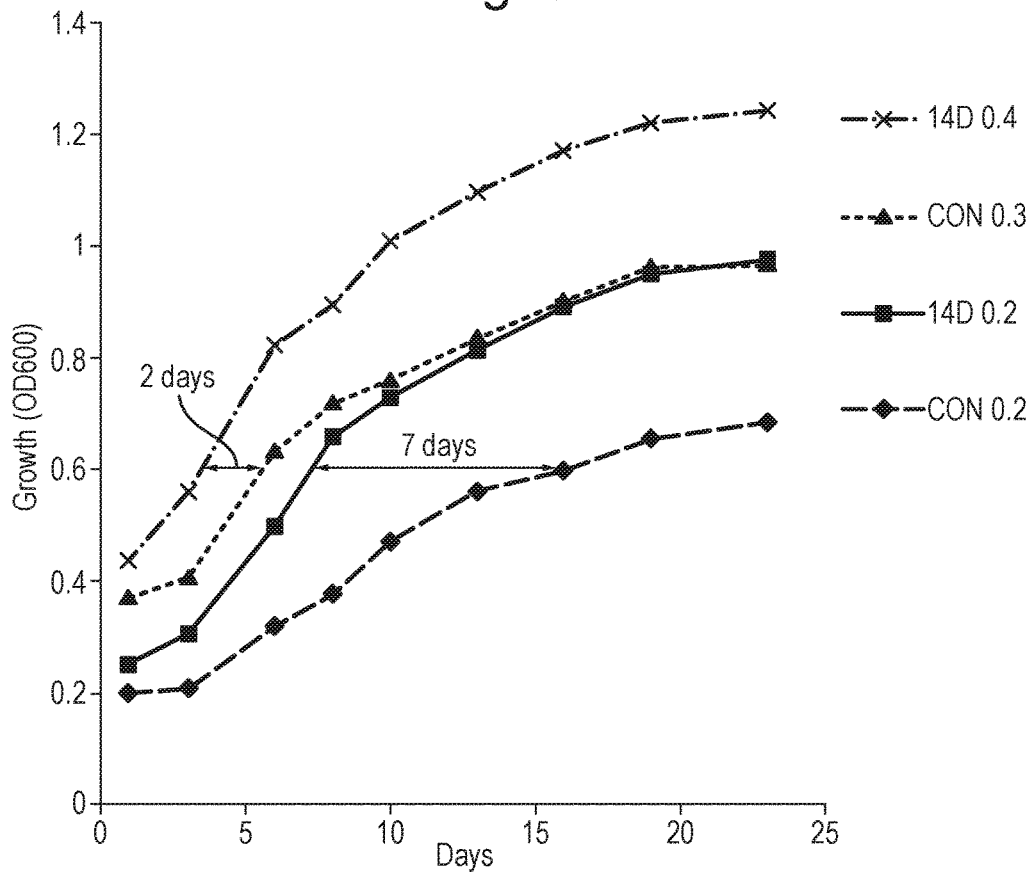
FIG. 3 shows the effects of TiKa 14D on cultures with different starting optical densities.

Results are presented in FIG. 3. As shown in this Figure, at a starting $OD_{600}$ of 0.2 TiKa 14D reduced the time to reach an $OD_{600}$ of 0.6 by 7 days relative to a control without the supplement. At a starting $OD_{600}$ of approximately 0.4, TiKa 14D reduced the time to reach an $OD_{600}$ of 0.6 by 2 days relative to the control without the supplement.

Example 4

Figure 4:
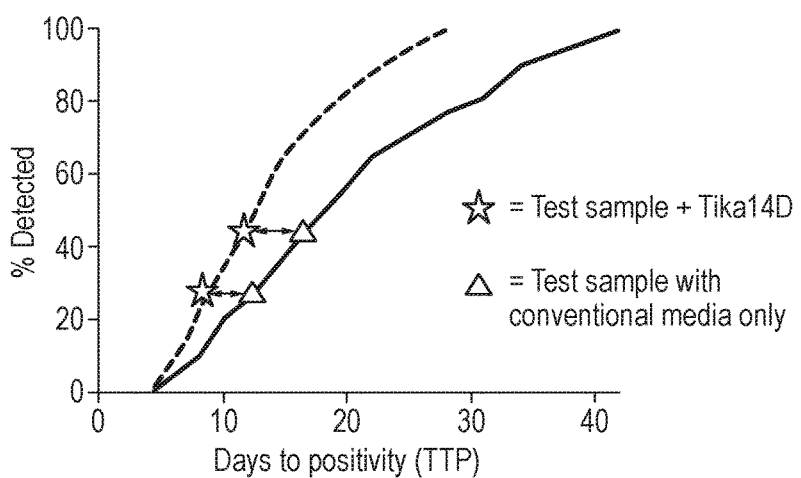
FIG. 4 shows the expected Time to Positivity for a test sample with TiKa 14D and for a control sample with conventional medium.

The time to positivity (the time from culture incubation to growth detection) was also determined. FIG. 4 presents a graph showing expected Time to Positivity (TTP) relative to % of all samples likely to be detected using BacTAlert (Biomerieux, France) commercial liquid media system (solid line) [reference: Tyrell et al. J Clin Microbiol. 2012 October; 50(10):3275-82], including projected graph (broken line) derived from selected test inocula comprising different loads of MTB added in parallel to media with and without TiKa14D. Results show TTP was decreased in TiKa supplemented media (compared to control media) and that the relative intensity of this effect increased as inoculum dose decreased.

Example 5

TiKa 14D and TiKa 102 were tested to identify the optimum concentration of supplement. Results are presented in FIGS. 5A and B for concentrations up to 80 µg/ml. As shown in FIG. 5A, for TiKa 14D the optimum concentration was identified to be 20 µg/ml and for TiKa 102 the optimum concentration was identified to be 40 µg/ml. Above the optimum concentration, the lag phase was still improved relative to the control without supplement, and the doubling time was still also reduced relative to the control. Below the optimum concentration, the lag phase was either not affected (10 µg/ml of TiKa 14D) or was inhibited relative to the control (slightly for TiKa 14D at 5 µg/ml and for TiKa 102 at 20 µg/ml). Below the optimum, the effects on the rate of division were decreased proportionally.

(Note that adding TiKa immediately increased initial $OD_{600}$, shifting baseline upwards relative to control. This was however, non-specific, as the shift was constant and proportional to the concentration of added TiKa)

Example 6

TiKa activity has been demonstrated in the following liquid media:
1. BacTAlert MP medium (Biomerieux, France);
2. MGIT960 medium (Becton Dickinson, USA);
3. Middlebrook 7H9 modified medium (reference: Pozzato et al. J. Microbiol. Methods. 2011 March; 84(3): 413-7)); and
4. Middlebrook 7H9 modified medium plus 0.5% sodium pyruvate (Sigma, UK)

TiKa activity has also been demonstrated in the following solid media: POZ-A medium: Middlebrook 7H9 modified medium (as above) with added 1.6% electrophoresis agarose (Sigma, UK). Results in this medium are shown in FIG. 6.

APPENDIX

| SEQ ID NO | Sequence |
|---|---|
| 1 | RKWKIKWYW |
| 2 | RLWWKIWLK |
| 3 | WKWRVRVTI |
| 4 | RWWRKIWKW |
| 5 | FFIYVWRRR |
| 6 | YRLRVKWKW |
| 7 | RIRRWKFRW |
| 8 | RQRRVVIWW |
| 9 | KRRWRIWLV |
| 10 | RTKKWIVWI |
| 11 | LRRWIRIRW |
| 12 | RRRIKIRWY |
| 13 | YKWKIRFKR |
| 14 | WKIVFWWRR |
| 15 | RRWRVIVKW |
| 16 | RLKRWWKFL |
| 17 | KFKWWRMLI |
| 18 | WKWLKKWIK |
| 19 | WRKFWKYLK |
| 20 | KWKWWWRKI |
| 21 | RRWWRWVVW |
| 22 | IRMRIRVLL |
| 23 | RWWIRIRWH |
| 24 | LKRRWKWWI |
| 25 | KRKKRFKWW |
| 26 | RRRWWKLMM |
| 27 | RLWWWWRRK |
| 28 | RKFRWWVIR |
| 29 | RWRWWWRVY |
| 30 | WFKAIRWWGR |
| 31 | FIKWKFRWWKWRK |
| 32 | HQFRFRFRVRRK |
| 33 | ILPWKWRWWKWRR |
| 34 | ILRWKWRWWRWRR |
| 35 | KIWWWWRKR |
| 36 | KRWWKWWRR |
| 37 | KRWWRKWWR |
| 38 | KRWWWWRFR |
| 39 | LRFILWWKR |
| 40 | NWRKLYRRK |
| 41 | RIKRWWWWR |
| 42 | RLRRIVVIRVFR |
| 43 | RLWRIVVIRVKR |
| 44 | RRWKIVVIRWRR |
| 45 | RRWWKWWWR |
| 46 | RRYHWRIYI |
| 47 | RWRRKWWWW |
| 48 | RWWRWRKWW |
| 49 | VRLRIRVRVIRK |
| 50 | YKFRWRIYI |
| 51 | FIKWKKRWWKKRT |
| 52 | FIKWRFRRWKKRT |
| 53 | FIKWRSRWWKKRT |
| 54 | FIKWRFRRWKKRK |
| 55 | FIKWKFRPWKKRT |
| 56 | FIKRKSRWWKWRT |
| 57 | ILKWKRKWWKWFR |
| 58 | ILKWKKGWWKWFR |
| 59 | ILKWKRKWWKWRR |
| 60 | ILKWKIPKWKWFR |
| 61 | ILKWKTKWWKWFR |
| 62 | ILKWKMFKWKWFR |
| 63 | ILPWKWPWWPWRR |
| 64 | RLARIVVIRVAR |
| 65 | RGARIVVIRVAR |

APPENDIX-continued

| SEQ ID NO | Sequence |
|---|---|
| 66 | RRARIVVIRVAR |
| 67 | RLWRIVVIRVAR |
| 68 | RLRRIVVIRVAR |
| 69 | RRWRIVVIRVRR |
| 70 | RLARIVVIRVRR |
| 71 | RLWRIVVIRVKR |
| 72 | RLARIVVIRWAR |
| 73 | RWRRWKWWL |
| 74 | KRWWKWWRR |
| 75 | FRRWWKWFK |
| 76 | VRWRIRVAVIRA |
| 77 | VRLRIRVAVIRA |
| 78 | LLGDFFRKSKEKIGKEFKRIVQRIKDFLRNLVPRTES |
| 79 | RRWKIVVIRWRR |
| 80 | KLWWIVHRRW |
| 81 | RLARIVPIRVAR |
| 86 | RRWRIVVIRVRR-bA-bA-C |
| 87 | RRWRIVVIRVRR-bA-bA-C(Meth) |
| 88 | KRWRIRVRVIRK-bA-bA-C |
| 89 | KRWRIRVRVIRK-bA-bA-C(Meth) |
| 90 | KRWWKWIRW-bA-bA-C |
| 91 | KRWWKWIRW-bA-bA-C(Meth) |
| 92 | RRWKIVVIRWRR |

APPENDIX-continued

| SEQ ID NO | Sequence |
|---|---|
| 93 | FITC-bA-bA-bA-GATPEDLNQKLS |
| 94 | FITC-bA-bA-bA-RRWKIVVIRWRR |
| 95 | FITC-bA-bA-bA-RLARIVPIRVAR |
| 96 | RWWKIWVIRWWR |
| 97 | RLCRIVVIRVCR |
| 98 | VRLRIRVWVIRA |
| 99 | KLWWIVHRRW |
| 100 | HQWRIRVAVRRH |
| 101 | RLARIVPIRVAR-BB-K(biotin) |
| 102 | RRWRIVVIRVRR-BB-K(biotin) |
| 103 | RLARIVVIRVAR-BB-K(biotin) |
| 104 | ILPWKWPWWPWRR-BB-K(biotin) |
| 108 | KLWWMIRRW |
| 110 | VQLRIRVAVIRA |
| 111 | KTCENLADDY |
| 112 | FIKWKFRWTKWRK |
| 113 | FIVWKFRWWKWRK |
| 114 | FIKWKFRWSKWRK |
| 115 | FIKWKFRWVKWRK |
| 116 | FIKWKFRWWKWRK |
| 117 | ILKWKWPWWKWRR |

-bA-bA-C beta-alanine, beta-alanine, cysteine
-BB-K(biotin) beta-alanine, beta-alanine, lysine with biotin
-bA-bA-C(Meth) beta-alanine, beta-alanine, methyl cysteine
FITC Fluorescein isothiocynate

The invention claimed is:

1. A method of enhancing the growth of cells of a slow-growing Mycobacterial species, comprising culturing the cells in a growth medium comprising an antimicrobial peptide up to 20 amino acids in length and comprising SEQ ID NO:14, a D-enantiomer of SEQ ID NO:14 or a sequence of L- and D-amino acids corresponding to SEQ ID NO:14, wherein the slow-growing Mycobacterial species is *Mycobacterium tuberculosis, Mycobacterium bovis*, or *Mycobacterium avium* and the *Mycobacterium avium* is *Mycobacterium avium* subspecies *paratuberculosis, Mycobacterium avium* subspecies *silvaticum, Mycobacterium avium* subspecies *hominissuis* or *Mycobacterium avium* subspecies *avium*.

2. The method of claim 1, wherein:
(a) the cells are from a sample of a subject suspected of having or known to have an infection with the slow-growing Mycobacterial species;
(b) the cells are from a sample of a subject suspected of having an infection with the slow-growing Mycobacterial species and a number of bacterial cells in an initial sample from the subject is too small to allow determination of bacterial species, subspecies or antibiotic resistance;
(c) the cells are from a sample of a subject suspected of having an infection with a slow-growing Mycobacterial species, a number of bacterial cells in an initial sample from the subject is too small to allow determination of bacterial species, subspecies or antibiotic resistance, and the method further comprises identifying one or more of the slow-growing Mycobacterial species, subspecies antibiotic resistance after the culturing of the cells; or
(d) the cells are from a sample of a subject known to have an infection with a slow-growing Mycobacterial species, and the method further comprises monitoring progress of the infection.

3. The method of claim 1, wherein the peptide consists of SEQ ID NO: 14.

4. The method of claim 1, wherein the peptide of up to 20 amino acids is a D-enantiomer.

5. The method of claim 1, wherein:
(a) the peptide is present at a final concentration of at least 10 μg/ml in the medium;
or
(b) the peptide is present at a final concentration of 10-100 μg/ml.

6. The method of claim 1, wherein the peptide comprises SEQ ID NO:14.

7. The method of claim 1, wherein the peptide comprises the D-enantiomer of SEQ ID NO:14.

8. The method of claim 1, wherein the peptide comprises D-amino acids and L-amino acids.

9. The method of claim 1, wherein the peptide of up to 20 amino acids is an L-enantiomer.

10. The method of claim 1, wherein the peptide consists of the D-enantiomer of SEQ ID NO:14.

11. The method of claim 1, wherein the peptide consists of the sequence of L- and D-amino acids corresponding to SEQ ID NO:14.

12. A method of diagnosing a suspected slow-growing Mycobacterial species infection in a subject, said method comprising:
(a) obtaining a sample from the subject suspected of having such an infection;
(b) growing cells of the slow-growing Mycobacterial species from the sample by culturing the cells in a growth medium comprising an antimicrobial peptide up to 20 amino acids in length and comprising SEQ ID NO:14, D-enantiomer of SEQ ID NO:14 or a mixture of L- and D-amino acids corresponding to SEQ ID NO:14; and,
(c) identifying the slow-growing Mycobacterial species, subspecies and/or antibiotic resistance after growth of the cells, and thereby diagnosing the infection, wherein the slow-growing Mycobacterial species is *Mycobacterium tuberculosis*, *Mycobacterium bovis*, or *Mycobacterium avium* and the *Mycobacterium avium* is *Mycobacterium avium* subspecies *paratuberculosis*, *Mycobacterium avium* subspecies *silvaticum*, *Mycobacterium avium* subspecies *hominissuis* or *Mycobacterium avium* subspecies *avium*.

13. A method of monitoring the progress of a slow-growing Mycobacterial species infection in a subject, said method comprising:
(a) obtaining a sample from the subject known to have such an infection;
(b) culturing cells from the sample in a growth medium comprising antimicrobial peptide up to 20 amino acids in length and comprising SEQ ID NO:14, D-enantiomer of SEQ ID NO:14 or a sequence of L- and D-amino acids corresponding to SEQ ID NO:14;
(c) analysing growth of the cells, or characteristics of the cells after growth; and
(d) repeating steps (a), (b) and (c),
wherein the slow-growing Mycobacterial species is *Mycobacterium tuberculosis*, *Mycobacterium bovis*, or *Mycobacterium avium* and the *Mycobacterium avium* is *Mycobacterium avium* subspecies *paratuberculosis*, *Mycobacterium avium* subspecies *silvaticum*, *Mycobacterium avium* subspecies *hominissuis* or *Mycobacterium avium* subspecies *avium*.

14. The method of claim 13, wherein the subject is treated with an anti-Mycobacterial agent after step (c) and before step (d).

* * * * *

SEQUENCE LISTING

<160> NUMBER OF SEQ ID NOS: 117

<210> SEQ ID NO 1
<211> LENGTH: 9
<212> TYPE: PRT
<213> ORGANISM: Artificial
<220> FEATURE:
<223> OTHER INFORMATION: Artificial peptide

<400> SEQUENCE: 1

Arg Lys Trp Lys Ile Lys Trp Tyr Trp
1               5

<210> SEQ ID NO 2
<211> LENGTH: 9
<212> TYPE: PRT
<213> ORGANISM: Artificial
<220> FEATURE:
<223> OTHER INFORMATION: Artificial peptide

<400> SEQUENCE: 2

```
Arg Leu Trp Trp Lys Ile Trp Leu Lys
1               5

<210> SEQ ID NO 3
<211> LENGTH: 9
<212> TYPE: PRT
<213> ORGANISM: Artificial
<220> FEATURE:
<223> OTHER INFORMATION: Artififical peptide

<400> SEQUENCE: 3

Trp Lys Trp Arg Val Arg Val Thr Ile
1               5

<210> SEQ ID NO 4
<211> LENGTH: 9
<212> TYPE: PRT
<213> ORGANISM: Artificial
<220> FEATURE:
<223> OTHER INFORMATION: Artificial peptide

<400> SEQUENCE: 4

Arg Trp Trp Arg Lys Ile Trp Lys Trp
1               5

<210> SEQ ID NO 5
<211> LENGTH: 9
<212> TYPE: PRT
<213> ORGANISM: Artificial
<220> FEATURE:
<223> OTHER INFORMATION: Artificial peptide

<400> SEQUENCE: 5

Phe Phe Ile Tyr Val Trp Arg Arg Arg
1               5

<210> SEQ ID NO 6
<211> LENGTH: 9
<212> TYPE: PRT
<213> ORGANISM: Artificial
<220> FEATURE:
<223> OTHER INFORMATION: Artificial peptide

<400> SEQUENCE: 6

Tyr Arg Leu Arg Val Lys Trp Lys Trp
1               5

<210> SEQ ID NO 7
<211> LENGTH: 9
<212> TYPE: PRT
<213> ORGANISM: Artificial
<220> FEATURE:
<223> OTHER INFORMATION: Artificial peptide

<400> SEQUENCE: 7

Arg Ile Arg Arg Trp Lys Phe Arg Trp
1               5

<210> SEQ ID NO 8
<211> LENGTH: 9
<212> TYPE: PRT
<213> ORGANISM: Artificial
<220> FEATURE:
<223> OTHER INFORMATION: Artificial peptide

<400> SEQUENCE: 8

Arg Gln Arg Arg Val Val Ile Trp Trp
```

```
<210> SEQ ID NO 9
<211> LENGTH: 9
<212> TYPE: PRT
<213> ORGANISM: Artificial
<220> FEATURE:
<223> OTHER INFORMATION: Artificial peptide

<400> SEQUENCE: 9

Lys Arg Arg Trp Arg Ile Trp Leu Val
1               5

<210> SEQ ID NO 10
<211> LENGTH: 9
<212> TYPE: PRT
<213> ORGANISM: Artificial
<220> FEATURE:
<223> OTHER INFORMATION: Artificial peptide

<400> SEQUENCE: 10

Arg Thr Lys Lys Trp Ile Val Trp Ile
1               5

<210> SEQ ID NO 11
<211> LENGTH: 9
<212> TYPE: PRT
<213> ORGANISM: Artificial
<220> FEATURE:
<223> OTHER INFORMATION: Artificial peptide

<400> SEQUENCE: 11

Leu Arg Arg Trp Ile Arg Ile Arg Trp
1               5

<210> SEQ ID NO 12
<211> LENGTH: 9
<212> TYPE: PRT
<213> ORGANISM: Artificial
<220> FEATURE:
<223> OTHER INFORMATION: Artificial peptide

<400> SEQUENCE: 12

Arg Arg Arg Ile Lys Ile Arg Trp Tyr
1               5

<210> SEQ ID NO 13
<211> LENGTH: 9
<212> TYPE: PRT
<213> ORGANISM: Artificial
<220> FEATURE:
<223> OTHER INFORMATION: Artificial peptide

<400> SEQUENCE: 13

Tyr Lys Trp Lys Ile Arg Phe Lys Arg
1               5

<210> SEQ ID NO 14
<211> LENGTH: 9
<212> TYPE: PRT
<213> ORGANISM: Artificial
<220> FEATURE:
<223> OTHER INFORMATION: Artificial peptide

<400> SEQUENCE: 14

Trp Lys Ile Val Phe Trp Trp Arg Arg
1               5
```

```
<210> SEQ ID NO 15
<211> LENGTH: 9
<212> TYPE: PRT
<213> ORGANISM: Artificial
<220> FEATURE:
<223> OTHER INFORMATION: Artificial peptide

<400> SEQUENCE: 15

Arg Arg Trp Arg Val Ile Val Lys Trp
1               5

<210> SEQ ID NO 16
<211> LENGTH: 9
<212> TYPE: PRT
<213> ORGANISM: Artificial
<220> FEATURE:
<223> OTHER INFORMATION: Artificial peptide

<400> SEQUENCE: 16

Arg Leu Lys Arg Trp Trp Lys Phe Leu
1               5

<210> SEQ ID NO 17
<211> LENGTH: 9
<212> TYPE: PRT
<213> ORGANISM: Artificial
<220> FEATURE:
<223> OTHER INFORMATION: Artificial peptide

<400> SEQUENCE: 17

Lys Phe Lys Trp Trp Arg Met Leu Ile
1               5

<210> SEQ ID NO 18
<211> LENGTH: 9
<212> TYPE: PRT
<213> ORGANISM: Artificial
<220> FEATURE:
<223> OTHER INFORMATION: Artificial peptide

<400> SEQUENCE: 18

Trp Lys Trp Leu Lys Lys Trp Ile Lys
1               5

<210> SEQ ID NO 19
<211> LENGTH: 9
<212> TYPE: PRT
<213> ORGANISM: Artificial
<220> FEATURE:
<223> OTHER INFORMATION: Artificial peptide

<400> SEQUENCE: 19

Trp Arg Lys Phe Trp Lys Tyr Leu Lys
1               5

<210> SEQ ID NO 20
<211> LENGTH: 9
<212> TYPE: PRT
<213> ORGANISM: Artificial
<220> FEATURE:
<223> OTHER INFORMATION: Artificial peptide

<400> SEQUENCE: 20

Lys Trp Lys Trp Trp Trp Arg Lys Ile
1               5
```

<210> SEQ ID NO 21
<211> LENGTH: 9
<212> TYPE: PRT
<213> ORGANISM: Artificial
<220> FEATURE:
<223> OTHER INFORMATION: Artificial peptide

<400> SEQUENCE: 21

Arg Arg Trp Trp Arg Trp Val Val Trp
1               5

<210> SEQ ID NO 22
<211> LENGTH: 9
<212> TYPE: PRT
<213> ORGANISM: Artificial
<220> FEATURE:
<223> OTHER INFORMATION: Artificial peptide

<400> SEQUENCE: 22

Ile Arg Met Arg Ile Arg Val Leu Leu
1               5

<210> SEQ ID NO 23
<211> LENGTH: 9
<212> TYPE: PRT
<213> ORGANISM: Artificial
<220> FEATURE:
<223> OTHER INFORMATION: Artificial peptide

<400> SEQUENCE: 23

Arg Trp Trp Ile Arg Ile Arg Trp His
1               5

<210> SEQ ID NO 24
<211> LENGTH: 9
<212> TYPE: PRT
<213> ORGANISM: Artificial
<220> FEATURE:
<223> OTHER INFORMATION: Artificial peptide

<400> SEQUENCE: 24

Leu Lys Arg Arg Trp Lys Trp Trp Ile
1               5

<210> SEQ ID NO 25
<211> LENGTH: 9
<212> TYPE: PRT
<213> ORGANISM: Artificial
<220> FEATURE:
<223> OTHER INFORMATION: Artificial peptide

<400> SEQUENCE: 25

Lys Arg Lys Lys Arg Phe Lys Trp Trp
1               5

<210> SEQ ID NO 26
<211> LENGTH: 9
<212> TYPE: PRT
<213> ORGANISM: Artificial
<220> FEATURE:
<223> OTHER INFORMATION: Artificial peptide

<400> SEQUENCE: 26

Arg Arg Arg Trp Trp Lys Leu Met Met
1               5

```
<210> SEQ ID NO 27
<211> LENGTH: 9
<212> TYPE: PRT
<213> ORGANISM: Artificial
<220> FEATURE:
<223> OTHER INFORMATION: Artificial peptide

<400> SEQUENCE: 27

Arg Leu Trp Trp Trp Trp Arg Arg Lys
1               5

<210> SEQ ID NO 28
<211> LENGTH: 9
<212> TYPE: PRT
<213> ORGANISM: Artificial
<220> FEATURE:
<223> OTHER INFORMATION: Artificial peptide

<400> SEQUENCE: 28

Arg Lys Phe Arg Trp Trp Val Ile Arg
1               5

<210> SEQ ID NO 29
<211> LENGTH: 9
<212> TYPE: PRT
<213> ORGANISM: Artificial
<220> FEATURE:
<223> OTHER INFORMATION: Artificial peptide

<400> SEQUENCE: 29

Arg Trp Arg Trp Trp Trp Arg Val Tyr
1               5

<210> SEQ ID NO 30
<211> LENGTH: 9
<212> TYPE: PRT
<213> ORGANISM: Artificial
<220> FEATURE:
<223> OTHER INFORMATION: Artificial peptide

<400> SEQUENCE: 30

Trp Phe Lys Met Arg Trp Trp Gly Arg
1               5

<210> SEQ ID NO 31
<211> LENGTH: 13
<212> TYPE: PRT
<213> ORGANISM: Artificial
<220> FEATURE:
<223> OTHER INFORMATION: Artificial peptide

<400> SEQUENCE: 31

Phe Ile Lys Trp Lys Phe Arg Trp Trp Lys Trp Arg Lys
1               5                   10

<210> SEQ ID NO 32
<211> LENGTH: 12
<212> TYPE: PRT
<213> ORGANISM: Artificial
<220> FEATURE:
<223> OTHER INFORMATION: Artificial peptide

<400> SEQUENCE: 32

His Gln Phe Arg Phe Arg Phe Arg Val Arg Arg Lys
1               5                   10

<210> SEQ ID NO 33
```

<211> LENGTH: 13
<212> TYPE: PRT
<213> ORGANISM: Artificial
<220> FEATURE:
<223> OTHER INFORMATION: Artificial peptide

<400> SEQUENCE: 33

Ile Leu Pro Trp Lys Trp Arg Trp Trp Lys Trp Arg Arg
1               5                   10

<210> SEQ ID NO 34
<211> LENGTH: 13
<212> TYPE: PRT
<213> ORGANISM: Artificial
<220> FEATURE:
<223> OTHER INFORMATION: Artificial peptide

<400> SEQUENCE: 34

Ile Leu Arg Trp Lys Trp Arg Trp Trp Arg Trp Arg Arg
1               5                   10

<210> SEQ ID NO 35
<211> LENGTH: 9
<212> TYPE: PRT
<213> ORGANISM: Artificial
<220> FEATURE:
<223> OTHER INFORMATION: Artificial peptide

<400> SEQUENCE: 35

Lys Ile Trp Trp Trp Trp Arg Lys Arg
1               5

<210> SEQ ID NO 36
<211> LENGTH: 9
<212> TYPE: PRT
<213> ORGANISM: Artificial
<220> FEATURE:
<223> OTHER INFORMATION: Artificial peptide

<400> SEQUENCE: 36

Lys Arg Trp Trp Lys Trp Trp Arg Arg
1               5

<210> SEQ ID NO 37
<211> LENGTH: 9
<212> TYPE: PRT
<213> ORGANISM: Artificial
<220> FEATURE:
<223> OTHER INFORMATION: Artificial peptide

<400> SEQUENCE: 37

Lys Arg Trp Trp Arg Lys Trp Trp Arg
1               5

<210> SEQ ID NO 38
<211> LENGTH: 9
<212> TYPE: PRT
<213> ORGANISM: Artificial
<220> FEATURE:
<223> OTHER INFORMATION: Artificial peptide

<400> SEQUENCE: 38

Lys Arg Trp Trp Trp Trp Arg Phe Arg
1               5

<210> SEQ ID NO 39
<211> LENGTH: 9

```
<212> TYPE: PRT
<213> ORGANISM: Artificial
<220> FEATURE:
<223> OTHER INFORMATION: Artificial peptide

<400> SEQUENCE: 39

Leu Arg Phe Ile Leu Trp Trp Lys Arg
1               5

<210> SEQ ID NO 40
<211> LENGTH: 9
<212> TYPE: PRT
<213> ORGANISM: Artificial
<220> FEATURE:
<223> OTHER INFORMATION: Artificial peptide

<400> SEQUENCE: 40

Asn Trp Arg Lys Leu Tyr Arg Arg Lys
1               5

<210> SEQ ID NO 41
<211> LENGTH: 9
<212> TYPE: PRT
<213> ORGANISM: Artificial
<220> FEATURE:
<223> OTHER INFORMATION: Artificial peptide

<400> SEQUENCE: 41

Arg Ile Lys Arg Trp Trp Trp Trp Arg
1               5

<210> SEQ ID NO 42
<211> LENGTH: 12
<212> TYPE: PRT
<213> ORGANISM: Artificial
<220> FEATURE:
<223> OTHER INFORMATION: Artificial peptide

<400> SEQUENCE: 42

Arg Leu Arg Arg Ile Val Val Ile Arg Val Phe Arg
1               5                   10

<210> SEQ ID NO 43
<211> LENGTH: 12
<212> TYPE: PRT
<213> ORGANISM: Artificial
<220> FEATURE:
<223> OTHER INFORMATION: Artificial peptide

<400> SEQUENCE: 43

Arg Leu Trp Arg Ile Val Val Ile Arg Val Lys Arg
1               5                   10

<210> SEQ ID NO 44
<211> LENGTH: 12
<212> TYPE: PRT
<213> ORGANISM: Artificial
<220> FEATURE:
<223> OTHER INFORMATION: Artificial peptide

<400> SEQUENCE: 44

Arg Arg Trp Lys Ile Val Val Ile Arg Trp Arg Arg
1               5                   10

<210> SEQ ID NO 45
<211> LENGTH: 9
<212> TYPE: PRT
```

```
<213> ORGANISM: Artificial
<220> FEATURE:
<223> OTHER INFORMATION: Artificial peptide

<400> SEQUENCE: 45

Arg Arg Trp Trp Lys Trp Trp Trp Arg
1               5

<210> SEQ ID NO 46
<211> LENGTH: 9
<212> TYPE: PRT
<213> ORGANISM: Artificial
<220> FEATURE:
<223> OTHER INFORMATION: Artificial peptide

<400> SEQUENCE: 46

Arg Arg Tyr His Trp Arg Ile Tyr Ile
1               5

<210> SEQ ID NO 47
<211> LENGTH: 9
<212> TYPE: PRT
<213> ORGANISM: Artificial
<220> FEATURE:
<223> OTHER INFORMATION: Artificial peptide

<400> SEQUENCE: 47

Arg Trp Arg Arg Lys Trp Trp Trp Trp
1               5

<210> SEQ ID NO 48
<211> LENGTH: 9
<212> TYPE: PRT
<213> ORGANISM: Artificial
<220> FEATURE:
<223> OTHER INFORMATION: Artificial peptide

<400> SEQUENCE: 48

Arg Trp Trp Arg Trp Arg Lys Trp Trp
1               5

<210> SEQ ID NO 49
<211> LENGTH: 12
<212> TYPE: PRT
<213> ORGANISM: Artificial
<220> FEATURE:
<223> OTHER INFORMATION: Artificial peptide

<400> SEQUENCE: 49

Val Arg Leu Arg Ile Arg Val Arg Val Ile Arg Lys
1               5                   10

<210> SEQ ID NO 50
<211> LENGTH: 9
<212> TYPE: PRT
<213> ORGANISM: Artificial
<220> FEATURE:
<223> OTHER INFORMATION: Artificial peptide

<400> SEQUENCE: 50

Tyr Lys Phe Arg Trp Arg Ile Tyr Ile
1               5

<210> SEQ ID NO 51
<211> LENGTH: 13
<212> TYPE: PRT
<213> ORGANISM: Artificial
```

```
<220> FEATURE:
<223> OTHER INFORMATION: Artificial peptide

<400> SEQUENCE: 51

Phe Ile Lys Trp Lys Lys Arg Trp Trp Lys Lys Arg Thr
1               5                   10

<210> SEQ ID NO 52
<211> LENGTH: 13
<212> TYPE: PRT
<213> ORGANISM: Artificial
<220> FEATURE:
<223> OTHER INFORMATION: Artificial peptide

<400> SEQUENCE: 52

Phe Ile Lys Trp Arg Phe Arg Arg Trp Lys Lys Arg Thr
1               5                   10

<210> SEQ ID NO 53
<211> LENGTH: 13
<212> TYPE: PRT
<213> ORGANISM: Artificial
<220> FEATURE:
<223> OTHER INFORMATION: Artificial peptide

<400> SEQUENCE: 53

Phe Ile Lys Trp Arg Ser Arg Trp Trp Lys Lys Arg Thr
1               5                   10

<210> SEQ ID NO 54
<211> LENGTH: 13
<212> TYPE: PRT
<213> ORGANISM: Artificial
<220> FEATURE:
<223> OTHER INFORMATION: Artificial peptide

<400> SEQUENCE: 54

Phe Ile Lys Trp Arg Phe Arg Arg Trp Lys Lys Arg Lys
1               5                   10

<210> SEQ ID NO 55
<211> LENGTH: 13
<212> TYPE: PRT
<213> ORGANISM: Artificial
<220> FEATURE:
<223> OTHER INFORMATION: Artificial peptide

<400> SEQUENCE: 55

Phe Ile Lys Trp Lys Phe Arg Pro Trp Lys Lys Arg Thr
1               5                   10

<210> SEQ ID NO 56
<211> LENGTH: 13
<212> TYPE: PRT
<213> ORGANISM: Artificial
<220> FEATURE:
<223> OTHER INFORMATION: Artificial peptide

<400> SEQUENCE: 56

Phe Ile Lys Arg Lys Ser Arg Trp Trp Lys Trp Arg Thr
1               5                   10

<210> SEQ ID NO 57
<211> LENGTH: 13
<212> TYPE: PRT
<213> ORGANISM: Artificial
<220> FEATURE:
```

<223> OTHER INFORMATION: Artificial peptide

<400> SEQUENCE: 57

Ile Leu Lys Trp Lys Arg Lys Trp Trp Lys Trp Phe Arg
1               5                   10

<210> SEQ ID NO 58
<211> LENGTH: 13
<212> TYPE: PRT
<213> ORGANISM: Artificial
<220> FEATURE:
<223> OTHER INFORMATION: Artificial peptide

<400> SEQUENCE: 58

Ile Leu Lys Trp Lys Lys Gly Trp Trp Lys Trp Phe Arg
1               5                   10

<210> SEQ ID NO 59
<211> LENGTH: 13
<212> TYPE: PRT
<213> ORGANISM: Artificial
<220> FEATURE:
<223> OTHER INFORMATION: Artificial peptide

<400> SEQUENCE: 59

Ile Leu Lys Trp Lys Arg Lys Trp Trp Lys Trp Arg Arg
1               5                   10

<210> SEQ ID NO 60
<211> LENGTH: 13
<212> TYPE: PRT
<213> ORGANISM: Artificial
<220> FEATURE:
<223> OTHER INFORMATION: Artificial peptide

<400> SEQUENCE: 60

Ile Leu Lys Trp Lys Ile Phe Lys Trp Lys Trp Phe Arg
1               5                   10

<210> SEQ ID NO 61
<211> LENGTH: 13
<212> TYPE: PRT
<213> ORGANISM: Artificial
<220> FEATURE:
<223> OTHER INFORMATION: Artificial peptide

<400> SEQUENCE: 61

Ile Leu Lys Trp Lys Thr Lys Trp Trp Lys Trp Phe Arg
1               5                   10

<210> SEQ ID NO 62
<211> LENGTH: 13
<212> TYPE: PRT
<213> ORGANISM: Artificial
<220> FEATURE:
<223> OTHER INFORMATION: Artificial peptide

<400> SEQUENCE: 62

Ile Leu Lys Trp Lys Met Phe Lys Trp Lys Trp Phe Arg
1               5                   10

<210> SEQ ID NO 63
<211> LENGTH: 13
<212> TYPE: PRT
<213> ORGANISM: Artificial
<220> FEATURE:
<223> OTHER INFORMATION: Artificial peptide

<400> SEQUENCE: 63

Ile Leu Pro Trp Lys Trp Pro Trp Trp Pro Trp Arg Arg
1               5                   10

<210> SEQ ID NO 64
<211> LENGTH: 12
<212> TYPE: PRT
<213> ORGANISM: Artificial
<220> FEATURE:
<223> OTHER INFORMATION: Artificial peptide

<400> SEQUENCE: 64

Arg Leu Ala Arg Ile Val Val Ile Arg Val Ala Arg
1               5                   10

<210> SEQ ID NO 65
<211> LENGTH: 12
<212> TYPE: PRT
<213> ORGANISM: Artificial
<220> FEATURE:
<223> OTHER INFORMATION: Artificial peptide

<400> SEQUENCE: 65

Arg Gly Ala Arg Ile Val Val Ile Arg Val Ala Arg
1               5                   10

<210> SEQ ID NO 66
<211> LENGTH: 12
<212> TYPE: PRT
<213> ORGANISM: Artificial
<220> FEATURE:
<223> OTHER INFORMATION: Artificial peptide

<400> SEQUENCE: 66

Arg Arg Ala Arg Ile Val Val Ile Arg Val Ala Arg
1               5                   10

<210> SEQ ID NO 67
<211> LENGTH: 12
<212> TYPE: PRT
<213> ORGANISM: Artificial
<220> FEATURE:
<223> OTHER INFORMATION: Artificial peptide

<400> SEQUENCE: 67

Arg Leu Trp Arg Ile Val Val Ile Arg Val Ala Arg
1               5                   10

<210> SEQ ID NO 68
<211> LENGTH: 12
<212> TYPE: PRT
<213> ORGANISM: Artificial
<220> FEATURE:
<223> OTHER INFORMATION: Artificial peptide

<400> SEQUENCE: 68

Arg Leu Arg Arg Ile Val Val Ile Arg Val Ala Arg
1               5                   10

<210> SEQ ID NO 69
<211> LENGTH: 12
<212> TYPE: PRT
<213> ORGANISM: Artificial
<220> FEATURE:
<223> OTHER INFORMATION: Artificial peptide

<400> SEQUENCE: 69

Arg Arg Trp Arg Ile Val Val Ile Arg Val Arg Arg
1               5                   10

<210> SEQ ID NO 70
<211> LENGTH: 12
<212> TYPE: PRT
<213> ORGANISM: Artificial
<220> FEATURE:
<223> OTHER INFORMATION: Artificial peptide

<400> SEQUENCE: 70

Arg Leu Ala Arg Ile Val Val Ile Arg Val Arg Arg
1               5                   10

<210> SEQ ID NO 71
<211> LENGTH: 12
<212> TYPE: PRT
<213> ORGANISM: Artificial
<220> FEATURE:
<223> OTHER INFORMATION: Artificial peptide

<400> SEQUENCE: 71

Arg Leu Trp Arg Ile Val Val Ile Arg Val Lys Arg
1               5                   10

<210> SEQ ID NO 72
<211> LENGTH: 12
<212> TYPE: PRT
<213> ORGANISM: Artificial
<220> FEATURE:
<223> OTHER INFORMATION: Artificial peptide

<400> SEQUENCE: 72

Arg Leu Ala Arg Ile Val Val Ile Arg Trp Ala Arg
1               5                   10

<210> SEQ ID NO 73
<211> LENGTH: 9
<212> TYPE: PRT
<213> ORGANISM: Artificial
<220> FEATURE:
<223> OTHER INFORMATION: Artificial peptide

<400> SEQUENCE: 73

Arg Trp Arg Arg Trp Lys Trp Trp Leu
1               5

<210> SEQ ID NO 74
<211> LENGTH: 9
<212> TYPE: PRT
<213> ORGANISM: Artificial
<220> FEATURE:
<223> OTHER INFORMATION: Artificial peptide

<400> SEQUENCE: 74

Lys Arg Trp Trp Lys Trp Trp Arg Arg
1               5

<210> SEQ ID NO 75
<211> LENGTH: 9
<212> TYPE: PRT
<213> ORGANISM: Artificial
<220> FEATURE:
<223> OTHER INFORMATION: Artificial peptide

<400> SEQUENCE: 75

```
Phe Arg Arg Trp Trp Lys Trp Phe Lys
1               5

<210> SEQ ID NO 76
<211> LENGTH: 12
<212> TYPE: PRT
<213> ORGANISM: Artificial
<220> FEATURE:
<223> OTHER INFORMATION: Artificial peptide

<400> SEQUENCE: 76

Val Arg Trp Arg Ile Arg Val Ala Val Ile Arg Ala
1               5                   10

<210> SEQ ID NO 77
<211> LENGTH: 12
<212> TYPE: PRT
<213> ORGANISM: Artificial
<220> FEATURE:
<223> OTHER INFORMATION: Artificial peptide

<400> SEQUENCE: 77

Val Arg Leu Arg Ile Arg Val Ala Val Ile Arg Ala
1               5                   10

<210> SEQ ID NO 78
<211> LENGTH: 37
<212> TYPE: PRT
<213> ORGANISM: Artificial
<220> FEATURE:
<223> OTHER INFORMATION: Artificial peptide

<400> SEQUENCE: 78

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
        35

<210> SEQ ID NO 79
<211> LENGTH: 12
<212> TYPE: PRT
<213> ORGANISM: Artificial
<220> FEATURE:
<223> OTHER INFORMATION: Artificial peptide

<400> SEQUENCE: 79

Arg Arg Trp Lys Ile Val Val Ile Arg Trp Arg Arg
1               5                   10

<210> SEQ ID NO 80
<211> LENGTH: 9
<212> TYPE: PRT
<213> ORGANISM: Artificial
<220> FEATURE:
<223> OTHER INFORMATION: Artificial peptide

<400> SEQUENCE: 80

Lys Leu Trp Trp Met Ile Arg Arg Trp
1               5

<210> SEQ ID NO 81
<211> LENGTH: 12
<212> TYPE: PRT
```

```
<213> ORGANISM: Artificial
<220> FEATURE:
<223> OTHER INFORMATION: Artificial peptide

<400> SEQUENCE: 81

Arg Leu Ala Arg Ile Val Pro Ile Arg Val Ala Arg
1               5                   10

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (13)..(14)
<223> OTHER INFORMATION: bAla

<400> SEQUENCE: 86

Arg Arg Trp Arg Ile Val Val Ile Arg Val Arg Arg Xaa Xaa Cys
1               5                   10                  15

<210> SEQ ID NO 87
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (13)..(14)
<223> OTHER INFORMATION: bAla
<220> FEATURE:
<221> NAME/KEY: MOD_RES
<222> LOCATION: (15)..(15)
<223> OTHER INFORMATION: METHYLATION

<400> SEQUENCE: 87

Arg Arg Trp Arg Ile Val Val Ile Arg Val Arg Arg Xaa Xaa Cys
1               5                   10                  15

<210> SEQ ID NO 88
<211> LENGTH: 15
<212> TYPE: PRT
```

<213> ORGANISM: Artificial
<220> FEATURE:
<223> OTHER INFORMATION: Artificial peptide
<220> FEATURE:
<221> NAME/KEY: MOD_RES
<222> LOCATION: (13)..(14)
<223> OTHER INFORMATION: bAla

<400> SEQUENCE: 88

Lys Arg Trp Arg Ile Arg Val Arg Val Ile Arg Lys Xaa Xaa Cys
1               5                   10                  15

<210> SEQ ID NO 89
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (13)..(14)
<223> OTHER INFORMATION: bAla
<220> FEATURE:
<221> NAME/KEY: MOD_RES
<222> LOCATION: (15)..(15)
<223> OTHER INFORMATION: METHYLATION

<400> SEQUENCE: 89

Lys Arg Trp Arg Ile Arg Val Arg Val Ile Arg Lys Xaa Xaa Cys
1               5                   10                  15

<210> SEQ ID NO 90
<211> LENGTH: 12
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (10)..(11)
<223> OTHER INFORMATION: bAla

<400> SEQUENCE: 90

Lys Arg Trp Trp Lys Trp Ile Arg Trp Xaa Xaa Cys
1               5                   10

<210> SEQ ID NO 91
<211> LENGTH: 12
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (10)..(11)
<223> OTHER INFORMATION: bAla
<220> FEATURE:
<221> NAME/KEY: MOD_RES
<222> LOCATION: (12)..(12)
<223> OTHER INFORMATION: METHYLATION

<400> SEQUENCE: 91

Lys Arg Trp Trp Lys Trp Ile Arg Trp Xaa Xaa Cys
1               5                   10

<210> SEQ ID NO 92
<211> LENGTH: 12
<212> TYPE: PRT
<213> ORGANISM: Artificial
<220> FEATURE:
<223> OTHER INFORMATION: Artificial peptide

```
<400> SEQUENCE: 92

Arg Arg Trp Lys Ile Val Val Ile Arg Trp Arg Arg
1               5                   10

<210> SEQ ID NO 93
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (1)..(3)
<223> OTHER INFORMATION: bAla
<220> FEATURE:
<221> NAME/KEY: MOD_RES
<222> LOCATION: (1)..(1)
<223> OTHER INFORMATION: FITC tag

<400> SEQUENCE: 93

Xaa Xaa Xaa Gly Ala Thr Pro Glu Asp Leu Asn Gln Lys Leu Ser
1               5                   10                  15

<210> SEQ ID NO 94
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (1)..(3)
<223> OTHER INFORMATION: bAla
<220> FEATURE:
<221> NAME/KEY: MOD_RES
<222> LOCATION: (1)..(1)
<223> OTHER INFORMATION: FITC tag

<400> SEQUENCE: 94

Xaa Xaa Xaa Arg Arg Trp Lys Ile Val Val Ile Arg Trp Arg Arg
1               5                   10                  15

<210> SEQ ID NO 95
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (1)..(3)
<223> OTHER INFORMATION: bAla
<220> FEATURE:
<221> NAME/KEY: MOD_RES
<222> LOCATION: (1)..(1)
<223> OTHER INFORMATION: FITC tag

<400> SEQUENCE: 95

Xaa Xaa Xaa Arg Leu Ala Arg Ile Val Pro Ile Arg Val Ala Arg
1               5                   10                  15

<210> SEQ ID NO 96
<211> LENGTH: 12
<212> TYPE: PRT
<213> ORGANISM: Artificial
<220> FEATURE:
<223> OTHER INFORMATION: Artificial peptide

<400> SEQUENCE: 96
```

```
Arg Trp Trp Lys Ile Trp Val Ile Arg Trp Trp Arg
1               5                   10
```

<210> SEQ ID NO 97
<211> LENGTH: 12
<212> TYPE: PRT
<213> ORGANISM: Artificial
<220> FEATURE:
<223> OTHER INFORMATION: Artificial peptide

<400> SEQUENCE: 97

```
Arg Leu Cys Arg Ile Val Val Ile Arg Val Cys Arg
1               5                   10
```

<210> SEQ ID NO 98
<211> LENGTH: 12
<212> TYPE: PRT
<213> ORGANISM: Artificial
<220> FEATURE:
<223> OTHER INFORMATION: Artificial peptide

<400> SEQUENCE: 98

```
Val Arg Leu Arg Ile Arg Val Trp Val Ile Arg Ala
1               5                   10
```

<210> SEQ ID NO 99
<211> LENGTH: 9
<212> TYPE: PRT
<213> ORGANISM: Artificial
<220> FEATURE:
<223> OTHER INFORMATION: Artificial peptide

<400> SEQUENCE: 99

```
Lys Leu Trp Trp Met Ile Arg Arg Trp
1               5
```

<210> SEQ ID NO 100
<211> LENGTH: 12
<212> TYPE: PRT
<213> ORGANISM: Artificial
<220> FEATURE:
<223> OTHER INFORMATION: Artificial peptide

<400> SEQUENCE: 100

```
His Gln Trp Arg Ile Arg Val Ala Val Arg Arg His
1               5                   10
```

<210> SEQ ID NO 101
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (13)..(14)
<223> OTHER INFORMATION: bAla
<220> FEATURE:
<221> NAME/KEY: MOD_RES
<222> LOCATION: (15)..(15)
<223> OTHER INFORMATION: with biotin

<400> SEQUENCE: 101

```
Arg Leu Ala Arg Ile Val Pro Ile Arg Val Ala Arg Xaa Xaa Lys
1               5                   10                  15
```

<210> SEQ ID NO 102
<211> LENGTH: 15

```
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (13)..(14)
<223> OTHER INFORMATION: bAla
<220> FEATURE:
<221> NAME/KEY: MOD_RES
<222> LOCATION: (15)..(15)
<223> OTHER INFORMATION: with biotin

<400> SEQUENCE: 102

Arg Arg Trp Arg Ile Val Val Ile Arg Val Arg Arg Xaa Xaa Lys
1               5                   10                  15

<210> SEQ ID NO 103
<211> LENGTH: 15
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (13)..(14)
<223> OTHER INFORMATION: bAla
<220> FEATURE:
<221> NAME/KEY: MOD_RES
<222> LOCATION: (15)..(15)
<223> OTHER INFORMATION: with biotin

<400> SEQUENCE: 103

Arg Leu Ala Arg Ile Val Val Ile Arg Val Ala Arg Xaa Xaa Lys
1               5                   10                  15

<210> SEQ ID NO 104
<211> LENGTH: 16
<212> TYPE: PRT
<213> ORGANISM: Artificial
<220> FEATURE:
<223> OTHER INFORMATION: Artificial peptide
<220> FEATURE:
<221> NAME/KEY: MOD_RES
<222> LOCATION: (14)..(15)
<223> OTHER INFORMATION: bAla
<220> FEATURE:
<221> NAME/KEY: MOD_RES
<222> LOCATION: (16)..(16)
<223> OTHER INFORMATION: with biotin

<400> SEQUENCE: 104

Ile Leu Pro Trp Lys Trp Pro Trp Trp Pro Trp Arg Arg Xaa Xaa Lys
1               5                   10                  15

<210> SEQ ID NO 105

<400> SEQUENCE: 105

000

<210> SEQ ID NO 106

<400> SEQUENCE: 106

000

<210> SEQ ID NO 107

<400> SEQUENCE: 107
```

000

```
<210> SEQ ID NO 108
<211> LENGTH: 9
<212> TYPE: PRT
<213> ORGANISM: Artificial
<220> FEATURE:
<223> OTHER INFORMATION: Artificial peptide

<400> SEQUENCE: 108

Lys Leu Trp Trp Met Ile Arg Arg Trp
1               5

<210> SEQ ID NO 109

<400> SEQUENCE: 109

000

<210> SEQ ID NO 110
<211> LENGTH: 12
<212> TYPE: PRT
<213> ORGANISM: Artificial
<220> FEATURE:
<223> OTHER INFORMATION: Artificial peptide

<400> SEQUENCE: 110

Val Gln Leu Arg Ile Arg Val Ala Val Ile Arg Ala
1               5                   10

<210> SEQ ID NO 111
<211> LENGTH: 10
<212> TYPE: PRT
<213> ORGANISM: Artificial
<220> FEATURE:
<223> OTHER INFORMATION: Artificial peptide

<400> SEQUENCE: 111

Lys Thr Cys Glu Asn Leu Ala Asp Asp Tyr
1               5                   10

<210> SEQ ID NO 112
<211> LENGTH: 13
<212> TYPE: PRT
<213> ORGANISM: Artificial
<220> FEATURE:
<223> OTHER INFORMATION: Artificial peptide

<400> SEQUENCE: 112

Phe Ile Lys Trp Lys Phe Arg Trp Thr Lys Trp Arg Lys
1               5                   10

<210> SEQ ID NO 113
<211> LENGTH: 13
<212> TYPE: PRT
<213> ORGANISM: Artificial
<220> FEATURE:
<223> OTHER INFORMATION: Artificial peptide

<400> SEQUENCE: 113

Phe Ile Val Trp Lys Phe Arg Trp Trp Lys Trp Arg Lys
1               5                   10

<210> SEQ ID NO 114
<211> LENGTH: 13
<212> TYPE: PRT
<213> ORGANISM: Artificial
```

```
<220> FEATURE:
<223> OTHER INFORMATION: Artificial peptide

<400> SEQUENCE: 114

Phe Ile Lys Trp Lys Phe Arg Trp Ser Lys Trp Arg Lys
1               5                   10

<210> SEQ ID NO 115
<211> LENGTH: 13
<212> TYPE: PRT
<213> ORGANISM: Artificial
<220> FEATURE:
<223> OTHER INFORMATION: Artificial peptide

<400> SEQUENCE: 115

Phe Ile Lys Trp Lys Phe Arg Trp Val Lys Trp Arg Lys
1               5                   10

<210> SEQ ID NO 116
<211> LENGTH: 13
<212> TYPE: PRT
<213> ORGANISM: Artificial
<220> FEATURE:
<223> OTHER INFORMATION: Artificial peptide

<400> SEQUENCE: 116

Phe Ile Lys Trp Lys Phe Arg Trp Trp Lys Trp Arg Lys
1               5                   10

<210> SEQ ID NO 117
<211> LENGTH: 13
<212> TYPE: PRT
<213> ORGANISM: Artificial
<220> FEATURE:
<223> OTHER INFORMATION: Artificial peptide

<400> SEQUENCE: 117

Ile Leu Lys Trp Lys Trp Pro Trp Trp Lys Trp Arg Arg
1               5                   10
```